US010392356B2

(12) United States Patent
Scanlan et al.

(10) Patent No.: US 10,392,356 B2
(45) Date of Patent: *Aug. 27, 2019

(54) DERIVATIVES OF SOBETIROME

(71) Applicant: OREGON HEALTH & SCIENCE UNIVERSITY, Portland, OR (US)

(72) Inventors: Thomas S. Scanlan, Portland, OR (US); Andrew Placzek, Portland, OR (US); Tapasree Banerji, West Linn, OR (US); Sky Ferrara, Portland, OR (US); James Matthew Meinig, Portland, OR (US)

(73) Assignee: OREGON HEALTH & SCIENCE UNIVERSITY, Portland, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 15/615,408

(22) Filed: Jun. 6, 2017

(65) Prior Publication Data

US 2018/0057472 A1 Mar. 1, 2018

Related U.S. Application Data

(63) Continuation of application No. 15/048,672, filed on Feb. 19, 2016, now Pat. No. 9,701,650.

(60) Provisional application No. 62/119,001, filed on Feb. 20, 2015.

(51) Int. Cl.
| | |
|---|---|
| *C07D 295/088* | (2006.01) |
| *C07D 205/04* | (2006.01) |
| *C07D 207/08* | (2006.01) |
| *C07D 211/22* | (2006.01) |
| *C07D 211/42* | (2006.01) |
| *C07D 211/44* | (2006.01) |
| *C07D 233/64* | (2006.01) |
| *C07D 309/10* | (2006.01) |
| *C07C 219/06* | (2006.01) |
| *C07C 229/36* | (2006.01) |
| *C07C 235/06* | (2006.01) |
| *C07C 237/08* | (2006.01) |
| *C07C 69/736* | (2006.01) |
| *C07H 13/04* | (2006.01) |
| *A61P 25/00* | (2006.01) |

(52) U.S. Cl.
CPC .......... *C07D 295/088* (2013.01); *A61P 25/00* (2018.01); *C07C 69/736* (2013.01); *C07C 219/06* (2013.01); *C07C 229/36* (2013.01); *C07C 235/06* (2013.01); *C07C 237/08* (2013.01); *C07D 205/04* (2013.01); *C07D 207/08* (2013.01); *C07D 211/22* (2013.01); *C07D 211/42* (2013.01); *C07D 211/44* (2013.01); *C07D 233/64* (2013.01); *C07D 309/10* (2013.01); *C07H 13/04* (2013.01); *C07B 2200/07* (2013.01); *C07C 2601/04* (2017.05)

(58) Field of Classification Search
CPC . C07D 295/088; C07D 219/06; C07D 205/04
See application file for complete search history.

(56) References Cited

U.S. PATENT DOCUMENTS

| | | | | |
|---|---|---|---|---|
| 5,883,294 | A * | 3/1999 | Scanlan | .................. C07C 59/70 560/52 |
| 9,701,650 | B2 * | 7/2017 | Scanlan | ............. C07D 295/088 |
| 2008/0124280 | A1 | 5/2008 | Mousa et al. | |
| 2009/0306225 | A1 | 12/2009 | Lichter et al. | |
| 2010/0303934 | A1 | 12/2010 | Soumyanath | |
| 2012/0004166 | A1 | 1/2012 | Keil et al. | |
| 2016/0244418 | A1 | 8/2016 | Scanlan et al. | |

FOREIGN PATENT DOCUMENTS

| | | |
|---|---|---|
| EP | 3259246 | 12/2017 |
| WO | 2006031922 A1 | 3/2006 |
| WO | 20080125724 A1 | 10/2008 |
| WO | 2016134292 A1 | 8/2016 |
| WO | 2017015360 | 1/2017 |
| WO | 2017201320 | 11/2017 |

OTHER PUBLICATIONS

Scanlan et al., "Sobetirome: a case history of bench-to-clinic drug discovery and development", Heart Fail Rev. 15, 2010, 177-182.
Grover et al., "Effects of the Thyroid Hormone Receptor Agonist GC-1 on Metabolic Rate and Cholesterol in Rats and Primates: Selective Actions Relative to 3,5,3'-Triiodo-L-Thyronine", Endocrinology 145(4), 2004, 1656-1661.
Takahashi et al., "In Vivo Evaluation of 1-Benzyl-4-aminoindole-Based Thyroid Hormone Receptor β Agonists: Importance of Liver Selectivity in Drug Discovery", Biol. Pharm. Bull. 37(3), 2014, 1103-1108.
Torst et al., "The Thyroid Hormone Receptor-β-Selective Agonist GC-1 Differentially Affects Plasma Lipids and Caridac Activity", Endocrinology, vol. 141, No. 9, 2000, 3057-3064.
Bernal, "Thyroid hormone receptors in brain development and function", Nature Clinical Practice Endocrinology & Metabolism 3, 2007, 249-259.
Oppenheimer et al., "Molecular Basis of Thyroid Hormone-Dependent Brain Development", Endocrine Reviews vol. 18, No. 4, 1997, 462-475.
Bernal, "Action of thyroid hormone in brain", J. Endocrinol. Invest. 25, 2002, 268-288.
Doran et al., "The Impact of P-Glycoprotein on the Disposition of Drugs Targeted for Indications of the Central Nervous system: Evaluation Using the MDR1A/1B Knockout Mouse Model", Drug Metabolism and Disposition vol. 33, No. 1, 2005, 165-174.

(Continued)

*Primary Examiner* — Pancham Bakshi
(74) *Attorney, Agent, or Firm* — Kilpatrick Townsend & Stockton LLP

(57) ABSTRACT

Ester derivatives of sobetirome with enhanced CNS distribution are disclosed.

11 Claims, 5 Drawing Sheets

(56) References Cited

OTHER PUBLICATIONS

Reichel, "The Role of Blood-Brain Barrier Studies in the Pharmaceutical Industry", Current Drug Metabolism 7, 2006, 183-203.
Boymond et al., "Preparation of Highly Functionalized Grignard Reagents by an Iodine-Magnesium Exchange Reaction and its Application in Solid-Phase Synthesis", Angew. Chem. Int. Ed. vol. 37, No. 12, 1998, 1701-1703.
Edgar et al., "An Efficient and Selective Method for the Preparation of Iodophenols", J. Org. Chem. 55, 1990, 5287-5291.
Penning et al., "Structure-Activity Relationship Studies on 1-[2-(4-Phenylphenozy)ethyl]pyrrolidine (SC-22716), a Potent Inhibitor of Leukotriene A4 (LTA4) Hydrolase", J. Med. Chem. 43, 2000, 721-735.
Mandal et al., "Pd-C-Induced Catalytic Transfer Hydrogenation with Triethylsilane", J. Org. Chem. 72, 2007, 6599-6601.
Smith et al., "Water soluble prodrug of a COX-2 selective inhibitor suitable for intravenous administration in models of cerebral ischemia", Bioorganic & Medicinal Chemistry Letters 15, 205, 3197-3200.
Lu et al., "An expedient sythesis of benzyl 2,3,4-tri-O-benzyl-β-D-glucopyranoside and benzyl 2,3,4-tri-O-benzyl-β-D-mannopyranoside", Carbohydrate Research 340, 2005, 1213-1217.
Scanlan, "Safety and Pharmacodynamic Study of Sobetirome in X-linked 1—Adrenoleukodystrophy (X-ALD). ClinicalTrials.gov, [retreieved from the Internet] Retrieved from—y—<https://clinicaltrials.gov/ct2/show/NCT01787578>.", Feb. 6, 2013; p. 1 purpose; 7/2-4, 11/7/2-4 p. 2, arms, experiment, detailed description.
Miller et al., "Primary-progressive multiple sclerosis", Lancet Neurology 6, 2007, 903-912.
Hafer-Macko et al., "Immune Attach on the Schwann Cell Surface in Acute Inflammatory Demyelinating Polyneuropathy", Annals of Neurology vol. 39, No. 5, 1996, 625-635.
Tangdenpaisal et al., "Synthesis of the thyroid hormone analog GC-1 via Bi(OTf)3-catalyzed benzylation", Tetrahedron, vol. 70, No. 38, Sep. 2014, pp. 6789-6795.
Link et al., "Photo-caged agonists of the nuclear receptors RARγ and TRβ provide unique time-dependent gene expression profiles for light-activated gene patterning", Bioorganic & Medicinal Chemistry 12, 2004, 5949-5959.
Nguyen et al., "Hammett Analysis of Selective Thyroid Hormone Receptor Modulators Reveals Structural and Electronic Requirements for Hormone Antagonists", J. Am. Chem. Soc. 127, 2005, 4599-4608.
Chiellini et al., "A high-affinity subtype-selective agonist ligand for the thyroid hormone receptor", Chemistry & Biology, vol. 5, 1998, pp. 299-306.
PCT/US2016/018732, "International Search Report and Written Opinion", Jun. 1, 2016, 15 pages.
U.S. Appl. No. 15/048,672, "Non-Final Office Action", dated Jul. 6, 2016, 17 pages.
U.S. Appl. No. 15/048,672, "Notice of Allowance", dated Mar. 6, 2017, 9 pages.
CONC2017/0009514, "Office Action", dated Nov. 16, 2017, 4 pages.
Chiellini et al., "Synthesis and Biological Activity of Novel Thyroid Hormone Analogues: 5'-Aryl Substituted GC-1 Derivatives", Bioorganic & Medicinal Chemistry, vol. 10, No. 2, 2002, pp. 333-346.
EP16753172.2, "Extended European Search Report", dated Aug. 30, 2018, 8 pages.
Ferrara et al., "Ester-to-Amide Rearrangement of Ethanolamine-Derived Prodrugs of Sobetirome with Increased Blood-Brain Barrier Penetration", Bioorg. & Med. Chem., vol. 25, No. 10, Mar. 23, 2017, pp. 2743-2753.
Nguyen et al., "Rational Design and Synthesis of a Novel Thyroid Hormone Antagonist That Blocks Coactivator Recruitment", J. Med. Chem. vol. 45, No. 15, 2002, pp. 3310-3320.
Placzek et al., "Sobetirome Prodrug Esters with Enhanced Blood-Brain Barrier Permeability", Bioorg. & Med. Chem., vol. 24, No. 22, Sep. 16, 2016, pp. 5842-5854.
Yoshihara et al., "A Designed Antagonist of the Thyroid Hormone Receptor", Bioorganic & Medicinal Chemistry Letters, vol. 11, No. 21, 2001, pp. 2821-2825.
PCT/US2019/017881, "International Search Report and Written Opinion", dated May 13, 2019, 9 pages.

* cited by examiner

DERIVATIVES OF SOBETIROME

ACKNOWLEDGEMENT OF GOVERNMENT SUPPORT

This invention was made with the support of the United States government under the terms of grant numbers RC4 DK090849 and R01 DK091539, both awarded by the National Institutes of Health. The United States government has certain rights to this invention.

FIELD

Generally, the field is medicinal compounds and pharmaceutical compositions. More specifically, the field involves derivatives of sobetirome with improved transit to the central nervous system.

BACKGROUND

There is increasing interest in activating specific thyroid hormone signaling pathways in the brain for the treatment of certain CNS diseases, in particular those that involve defects in remyelination (Fourcade S et al, *Mol Pharmacol* 63, 1296-1303 (2003) and Baxi E G et al, *Glia* 62, 1513-1529 (2014); both of which are incorporated by reference herein). Thyroid hormones T4 and T3 are not suitable as therapeutics for these indications as there is no therapeutic index for T4 and T3 separating the desired therapeutic effect from adverse effects associated with hyperthyroidism such as tachycardia, muscle wasting, and osteoporosis (Yen P M et al, *Physiol Rev* 81, 1097-1142 (2001); Yen P M et al, *Mol Cell Endocrinol* 246, 121-127 (2006); Biondi B and Klein I, *Endocrine* 24, 1-13 (2004); and Klein I and Ojamaa K, *Endocrinol Metab Clin North Am* 27, 51-62 (1998); all of which are incorporated by reference herein) This issue is potentially addressed by selective thyromimetics which are synthetic T3 agonists that show tissue selective thyroid hormone action (Joharapurkar A A et al, *J Med Chem* 55, 5649-5675 (2012); incorporated by reference herein.)

Sobetirome (also known as GC-1) is an example that has been studied extensively over the past 15 years (Scanlan T S, *Heart Fail Rev* 15, 177-182 (2010); incorporated by reference herein). Like T3, sobetirome affects LDL cholesterol lowering by stimulating hepatic cholesterol clearance mechanisms, but unlike T3, does so at doses that have no deleterious effect on heart, muscle, or bone (Grover G J et al, *Endocrinology* 145, 1656-1661 (2004); incorporated by reference herein). This therapeutic index supports the idea of testing sobetirome for efficacy in neurological disease models. However, distribution to the CNS is an essential property for such a thyromimetic to be useful as a therapeutic agent. Therefore sobetirome derivatives with improved CNS distribution are needed.

SUMMARY

Ester derivatives of sobetirome with the structure:

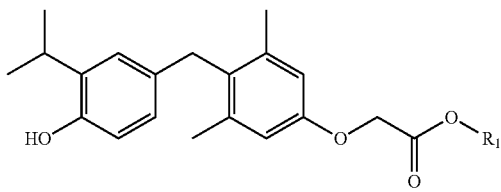

or any pharmaceutically acceptable salt thereof, wherein $R_1$ is alkyl or aryl. In further examples, $R_1$ is unsubstituted alkyl, substituted alkyl, heteroalkyl, substituted heteroalkyl, cycloalkyl, substituted cycloalkyl, heterocycloalkyl, substituted heterocycloalkyl, substituted aryl, heteroaryl, and substituted heteroaryl. In still further examples, $R_1$ can be ethyl, ethyltrimethylamino, ethylmorpholinyl, lysinyl, valinyl, phenylalaninyl, or glucosyl. In still further examples, $R_1$ can be alkylamino such as substituted alkylamino, cycloalkylamino or substituted cycloalkylamino. In additional examples, $R_1$ can be ethylamino, ethyl(N,N,N)-trimethylamino, ethylmorpholinyl, ethyl(N,N)-dimethylamino, 3-(N-methyl)azetidinyl, 4-pyrrolidinyl, 3-pyrrolidinyl, 2,2-dimethylethylamino, 3-(3-trifluoromethyl)azetidinyl, 2-pyrrolidinyl, 2-methylethylamino, 2-trifluoromethylamino, and N-methylethylamino.

In particular examples, the compounds have the structure:

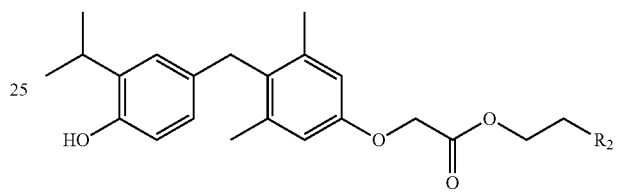

or any pharmaceutically acceptable salt thereof, wherein $R_2$ is amino or alkylamino. Examples of compounds of this structure include:

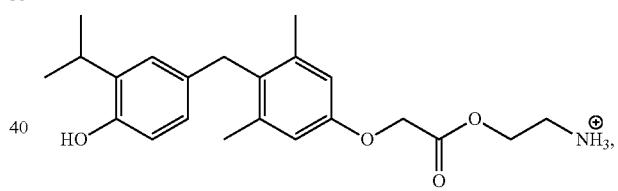

including any pharmaceutically acceptable salt thereof, including a halide salt.

Another particular example is a compound of the following structure:

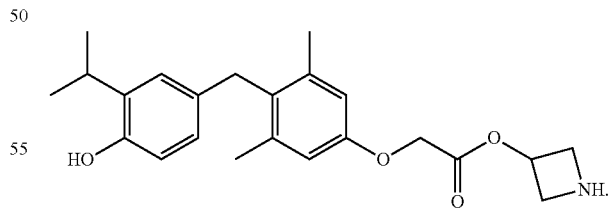

Also disclosed are pharmaceutical compositions that include an effective amount of the described compounds as an ingredient as well as a pharmaceutically acceptable carrier.

Also disclosed is the use of the compounds in the treatment of neurodegenerative disorders such as X-linked ALD and multiple sclerosis as well as methods of treating neurodegenerative disorders.

DETAILED DESCRIPTION

Definitions

Figure 1A:
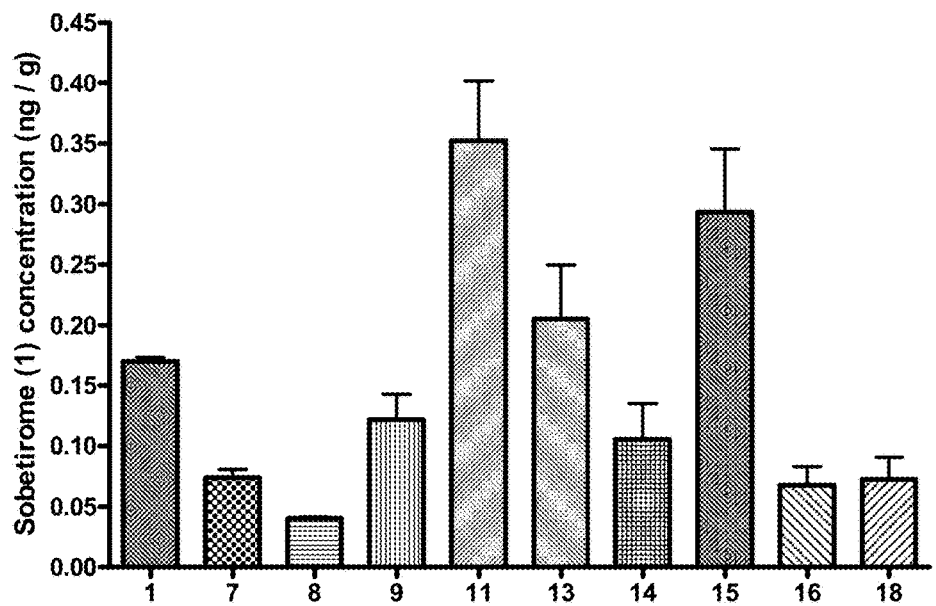
FIG. 1A is a bar graph depicting concentrations of the indicated compounds (ng/g) in the brain 30 minutes after intraperitoneal administration of sobetirome (compound 1) (1.5 μmol/kg) or prodrugs 7, 8, 9, 11, 13, 14, 15, 16, 18 (1.5 μmol/kg) in mice.

Unless specifically defined otherwise, the technical terms, as used herein, have their normal meaning as understood in the art. The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Variables such as R, including all subvariables thereof (such as $R_1$, $R_2$, etc.) used throughout the disclosure are the same variables as previously defined unless stated to the contrary.

Acute disseminated encephalomyelitis (ADEM): An immune-mediated demyelinating disease of the central nervous system. ADEM usually occurs following a viral infection, but may also appear following vaccination or following bacterial or parasitic infection. In some cases, ADEM develops spontaneously. The disease involves autoimmune demyelination, similar to multiple sclerosis, and is therefore considered a multiple sclerosis borderline disease. ADEM produces multiple inflammatory lesions in the brain and spinal cord, particularly in the white matter. The lesions are typically found in the subcortical and central white matter and cortical gray-white junction of both cerebral hemispheres, cerebellum, brainstem, and spinal cord, but periventricular white matter and gray matter of the cortex, thalami and basal ganglia may also be involved. When a patient suffers more than one demyelinating episode, the disease is referred to as recurrent disseminated encephalomyelitis or multiphasic disseminated encephalomyelitis.

Acute hemorrhagic leukoencephalitis (AHL or AHLE): A hyperacute and frequently fatal form of ADEM. This disease is also known as acute necrotizing encephalopathy (ANE), acute hemorrhagic encephalomyelitis (AHEM), acute necrotizing hemorrhagic leukoencephalitis (ANHLE), Weston-Hurst syndrome, or Hurst's disease.

Administration: Refers to providing a compound, a prodrug of a compound, or a pharmaceutical composition comprising a compound or prodrug as described herein. The compound or composition can be administered by another person to the subject or it can be self-administered by the subject.

Adult Refsum disease: An autosomal recessive neurological disease that is associated with the over-accumulation of phytanic acid in cells and tissues. Adult Refsum disease is divided into the adult Refsum disease 1 and adult Refsum disease 2 subtypes. Individuals with Refsum disease present with neurologic damage, cerebellar degeneration, and peripheral neuropathy. Onset is most commonly in childhood/adolescence with a progressive course, although periods of stagnation or remission occur. Symptoms also include ataxia, scaly skin (ichthyosis), difficulty hearing, and eye problems including cataracts and night blindness.

Alexander disease: A very rare, congenital demyelinating disease. The disease primarily affects infants and children, causing developmental delay and changes in physical characteristics. Alexander disease is a type of leukodystrophy.

Alkyl: a branched or unbranched saturated hydrocarbon group, such as, without limitation, methyl, ethyl, n-propyl, isopropyl, n-butyl, isobutyl, t-butyl, pentyl, hexyl, heptyl, octyl, nonyl, decyl, tetradecyl, hexadecyl, eicosyl, tetracosyl and the like. A lower alkyl group is a saturated branched or unbranched hydrocarbon having from 1 to 6 carbon atoms ($C_{1-6}$ alkyl). The term alkyl also encompasses cycloalkyls. Alkyl also encompasses substituted alkyls which are alkyl groups wherein one or more hydrogen atoms are replaced with a substituent such as, without limitation, alkyl, alkynyl, alkenyl, aryl, halide, nitro, amino, ester, ether, ketone, aldehyde, hydroxyl, carboxyl, cyano, amido, haloalkyl, haloalkoxy, or alkoxy. The term alkyl also encompasses heteroalkyls. A heteroalkyl contains at least one heteroatom such as nitrogen, oxygen, sulfur, or phosphorus replacing one or more of the carbons. Substituted heteroalkyls are also encompassed by the term alkyl.

Alkylamino: a heteroalkyl wherein one or more of the carbon atoms is replaced with a nitrogen. An alkylamino can be a straight chain, branched or cycloalkylamino. An alkylamino generally has the structure —$NX_1X_2$ or —$NX_1X_2X_3^+$ in which $X_1$, $X_2$, and $X_3$ are selected from H, a substituted alkyl, or an unsubstituted alkyl, as that term is defined above, provided that the group does not have the structure —$NH_2$ or —$NH_3^+$ Examples of alkylamino groups include the following structures: —$NHCH_3$, —$N(CH_3)_2$— $NH(CH_3)_2^+$—$N(CH3)_3^+$, $NHCH_2CH_3$, $NH_2CH_2CH_3^+$, $NCH_3CH_2CH_3$, $N(CH_2CH_3)_2$, $NHCH_3CH_2CH_3^+$. Alkylamino also encompasses heteroalkyls in which one or more of the carbon atoms is replaced with a nitrogen and, in addition, one or more of the other carbon atoms is replaced with another heteroatom such as oxygen, sulfur or phosphorus.

The term alkylamino also contemplates alkyl groups bonded to the nitrogen forming a bond with non-terminal carbons to form a cycloalkylamino structure, for example $X_1NHX_3$ wherein $X_1$ and $X_3$ are alkyl groups that form a covalent bond with one another. These include 4-member single nitrogen (azetidinyl), 5-member single nitrogen (pyrrolidinyl), or 6-member single nitrogen (piperidinyl) structures as well as double nitrogen structures, substituted cycloalkylamino structures, including $X_1NX_2X_3$ wherein $X_1$ and $X_3$ form a covalent bond and $X_2$ is alkyl. Alkylamino groups are further exemplified by a $CH_2CH_2NHR_2$ structure wherein $R_2$ is ethyl and forms a covalent bond with the first carbon to form a 4-member ring. Such a structure is exemplified by compound 15.

Alzheimer's disease: The most common form of dementia. Symptoms of Alzheimer's disease include memory loss, confusion, irritability, aggression, mood swings and trouble with language. This disease is characterized by the loss of neurons and synapses in the cerebral cortex and certain subcortical regions. The loss results in gross atrophy of the affected regions, including degeneration in the temporal lobe, and parts of the frontal cortex and cingulate gyrus. Amyloid plaques and neurofibrillary tangles are visible by microscopy in brains of those afflicted with this disease. The cause of Alzheimer's disease is unknown; however, several hypotheses exist, including that the disease is caused by age-related myelin breakdown in the brain.

Amide: a group with the structure —$CONX_1X_2$, wherein $X_1$ and $X_2$ are H or an organic group such as an alkyl or aryl group.

Aryl: any carbon-based aromatic group including, but not limited to, benzene, naphthalene, and phenyl. The term aryl also contemplates substituted aryls in which one or more of the hydrogens is substituted with one or more groups including but not limited to alkyl, alkynyl, alkenyl, aryl, halide, nitro, amino, ester, ether, ketone, aldehyde, hydroxy, carboxylic acid, cyano, amido, haloalkyl, haloalkoxy, or alkoxy. The term aryl also contemplates heteroaryls in which one or more of the carbons is replaced by a heteroatom. Examples of heteroatoms include, but are not limited to, nitrogen, oxygen, sulfur, and phosphorous. Substituted heteroaryls are also encompassed by the term aryl.

Balo concentric sclerosis: A demyelinating disease similar to standard multiple sclerosis, but with the particularity that the demyelinated tissues form concentric layers. Patients with this disease can survive and/or have spontaneous remission. Typically, the clinical course is primary progressive, but a relapsing-remitting course has been reported.

Canavan disease: An autosomal recessive degenerative disorder that causes progressive damage to nerve cells in the brain. Canavan disease is a leukodystrophy and is one of the most common degenerative cerebral diseases of infancy. This disease is also called Canavan-Van Bogaert-Bertrand disease, aspartoacylase deficiency and aminoacylase 2 deficiency.

Central pontine myelinolysis (CPM): A neurologic disease caused by severe damage of the myelin sheath of nerve cells in the brainstem, more precisely in the area termed the pons. The most common cause is the rapid correction of low blood sodium levels (hyponatremia). Frequently observed symptoms in this disorder are sudden para or quadraparesis, dysphagia, dysarthria, diplopia and loss of consciousness. The patient may experience locked-in syndrome where cognitive function is intact, but all muscles are paralyzed with the exception of eye blinking.

Cerebral palsy: A term used for a group of permanent, non-progressive movement disorders that cause physical disability. Cerebral palsy is caused by damage to the motor control centers of the developing brain and can occur during pregnancy, during childbirth, or after birth up to about age three. Patients with cerebral palsy exhibit damage to myelin sheaths.

Cerebrotendineous xanthomatosis: An inherited disorder associated with the deposition of a form of cholesterol (cholestanol) in the brain and other tissues and with elevated levels of cholesterol in plasma but with normal total cholesterol level. It is characterized by progressive cerebellar ataxia beginning after puberty and by juvenile cataracts, juvenile or infantile onset chronic diarrhea, childhood neurological deficit, and tendineous or tuberous xanthomas. This disorder is an autosomal recessive form of xanthomatosis. It falls within a group of genetic disorders called the leukodystrophies.

Chronic inflammatory demyelinating polyneuropathy (CIDP): An acquired immune-mediated inflammatory disorder of the peripheral nervous system. The disorder is sometimes called chronic relapsing polyneuropathy (CRP) or chronic inflammatory demyelinating polyradiculoneuropathy (because it involves the nerve roots). CIDP is closely related to Guillain-Barré syndrome and it is considered the chronic counterpart of that acute disease. Its symptoms are also similar to progressive inflammatory neuropathy. An asymmetrical variant of CIDP is known as Lewis-Sumner syndrome. The pathologic hallmark of the disease is loss of the myelin sheath.

Cycloalkyl: a non-aromatic carbon-based ring composed of at least three carbon atoms. Examples of cycloalkyl groups include, but are not limited to, cyclopropyl, cyclobutyl, cyclopentyl, and cyclohexyl. Cycloalkyls also encompass substituted cycloalkyls and heterocycloalkyls where at least one of the carbon atoms is replaced with a heteroatom such as nitrogen, sulfur or phosphorus. A heterocycloalkyl wherein one or more of the carbons is replaced with nitrogen is also termed a cycloalkylamino herein. The term also encompasses substituted heterocycloalkyls.

Demyelinating disease: Includes any disease of the nervous system in which myelin is damaged or lost, or in which the growth or development of the myelin sheath is impaired. Demyelination inhibits the conduction of signals in the affected nerves, causing impairment in sensation, movement, cognition, or other functions for which nerves are involved. Demyelinating diseases have a number of different causes and can be hereditary or acquired. In some cases, a demyelinating disease is caused by an infectious agent, an autoimmune response, a toxic agent or traumatic injury. In other cases, the cause of the demyelinating disease is unknown ("idiopathic") or develops from a combination of factors.

Derivative: a compound or portion of a compound that is derived from or is theoretically derivable from a parent compound.

Devic's syndrome: An autoimmune, inflammatory disorder in which a person's immune system attacks the optic nerves and spinal cord, which results in inflammation of the optic nerve (optic neuritis) and the spinal cord (myelitis). Spinal cord lesions lead to varying degrees of weakness or paralysis in the legs or arms, loss of sensation, and/or bladder and bowel dysfunction. Although inflammation may also affect the brain, the lesions are different from those observed in MS. Devic's syndrome is similar to MS in that the body's immune system attacks the myelin surrounding nerve cells. Unlike standard MS, the attacks are not believed to be mediated by the immune system's T cells but rather by antibodies called NMO-IgG. These antibodies target a protein called aquaporin 4 in the cell membranes of astrocytes which acts as a channel for the transport of water across the cell membrane. Devic's syndrome is also known as Devic's syndrome or neuromyelitis optica (NMO).

Diffuse myelinoclastic sclerosis: An uncommon neurodegenerative disease that presents clinically as pseudotumoral demyelinating lesions. It usually begins in childhood, affecting children between 5 and 14 years old; however, cases in adults are possible. This disease is considered one of the borderline forms of MS and is sometimes referred to as Schilder's disease.

Effective amount: a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

Encephalomyelitis: Inflammation of the brain and spinal cord.

Ester: a group with the structure —COOX where X is alkyl. For example an ethyl ester has the structure —COOCH$_2$CH$_3$.

Experimental autoimmune encephalomyelitis (EAE): An animal model of MS (for example, see Gold et al, *Brain* 129, 1953-1971 (2006). EAE animals exhibit characteristic plaques of tissue injury disseminated throughout the central nervous system. Plaques show infiltration of nervous tissue by lymphocytes, plasma cells, and macrophages, which cause destruction of the myelin sheaths that surround nerve cell axons in the brain and spinal cord. In some cases, EAE is induced by immunization of susceptible animals, such as mice, rats, guinea pigs, or non-human primates, with either myelin or various components of myelin. For example, EAE can be induced by immunization with components of the myelin sheath, such as myelin basic protein, proteolipid protein, or myelin oligodendrocyte glycoprotein (MOG). EAE is a useful and widely accepted model for studying mechanisms of autoimmune CNS tissue injury and for testing potential therapies for MS. EAE also includes "passive EAE" which is induced in the same manner in donor animals, but involves the transfer of activated T-cells harvested from the donor animal's lymph nodes to naïve recipient animals.

Guillain-Barré syndrome: An acute polyneuropathy, a disorder affecting the peripheral nervous system. Ascending paralysis, weakness beginning in the feet and hands and migrating towards the trunk, is the most typical symptom, and some subtypes cause change in sensation or pain, as well as dysfunction of the autonomic nervous system. It can cause life-threatening complications, in particular if the respiratory muscles are affected or if the autonomic nervous system is involved. This disease is usually triggered by an infection. Acute inflammatory demyelinating polyneuropathy (AIDP) is the most common subtype of this disease. Other subtypes of Guillain-Barré syndrome include Miller Fischer syndrome, acute motor axonal neuropathy (Chinese paralytic syndrome), acute motor sensory axonal neuropathy, acute panautonomic neuropathy, and Bickerstaff's brainstem encephalitis.

Heterocycle: A group that encompasses both heteroaryls and heterocycloalkyls heterocycles may be monocyclic or polycyclic rings. Exemplary heterocycles include, but are not limited to, azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl groups. The term also contemplates substituted heterocycles, including substituted forms of all the species above.

Hemorrhage: Bleeding or escape of blood from a vessel.

Hypoxia: The lack of oxygen supply to the tissues of the body below the normal level.

Idiopathic inflammatory demyelinating disease (IIDD): A broad spectrum of central nervous system disorders that can usually be differentiated on the basis of clinical, imaging, laboratory and pathological findings. Idiopathic inflammatory demyelinating diseases are sometimes known as borderline forms of multiple sclerosis. IIDD generally refers to a collection of multiple sclerosis variant diseases, including but not limited to, optic-spinal MS, Devic's disease, ADEM, acute hemorrhagic leukoencephalitis, Balo concentric sclerosis, Schilder disease, Marburg multiple sclerosis, tumefactive multiple sclerosis and solitary sclerosis.

Infantile Refsum disease: A peroxisome biogenesis disorder associated with deficiencies in the catabolism of very long chain fatty acids and branched chain fatty acids (such as phytanic acid) and plasmalogen biosynthesis. Infantile Refsum disease is a rare, autosomal recessive congenital disorder, and one of three peroxisome biogenesis disorders that belong to the Zellweger spectrum of peroxisome biogenesis disorders.

Injury: Refers to any type of physical damage to cells, tissues, or the body. In some cases, nervous system (e.g., CNS or PNS) injury results in demyelination and/or a demyelinating disease.

Ischemia: A vascular phenomenon in which a decrease in the blood supply to a bodily organ, tissue, or part is caused, for instance, by constriction or obstruction of one or more blood vessels. Ischemia sometimes results from vasoconstriction, thrombosis or embolism. Ischemia can lead to direct ischemic injury, tissue damage due to cell death caused by reduced oxygen supply. In some cases, ischemia can lead to demyelination.

Krabbe disease: A rare, often fatal degenerative disorder that affects the myelin sheath of the nervous system. It is a form of sphingolipidosis, as it involves dysfunctional metabolism of sphingolipids. This condition is inherited in an autosomal recessive pattern. Krabbe disease is also known as globoid cell leukodystrophy or galactosylceramide lipidosis.

Leber hereditary optic neuropathy: A mitochondrially inherited (transmitted from mother to offspring) degeneration of retinal ganglion cells (RGCs) and their axons that leads to an acute or subacute loss of central vision; this affects predominantly young adult males.

Leukodystrophy: Refers to a group of diseases that affects the growth or development of the myelin sheath.

Leukoencephalopathy: Any of a group of diseases affecting the white substance of the brain; can refer specifically to several diseases including, for example, "leukoencephalopathy with vanishing white matter" and "toxic leukoencephalopathy." Leukoencephalopathies are leukodystrophy-like diseases.

Marburg multiple sclerosis: A condition in which the central nervous system has multiple demyelinating lesions with atypical characteristics for those of standard multiple sclerosis. This disease is a borderline form of multiple sclerosis and is also known as tumefactive multiple sclerosis or fulminant multiple sclerosis. It is called tumefactive because the lesions are "tumor-like" and they mimic tumors clinically, radiologically and sometimes pathologically.

Marchiafava-Bignami disease: A progressive neurological disease characterized by corpus callosum demyelination and necrosis and subsequent atrophy. It is classically associated with chronic alcoholics.

Metachromatic leukodystrophy (MLD): A lysosomal storage disease that is commonly listed in the family of leukodystrophies, as well as in the sphingolipidoses as it affects the metabolism of sphingolipids. MLD is directly caused by a deficiency of the enzyme arylsulfatase A.

Multifocal motor neuropathy (MMN): A progressively worsening condition where muscles in the extremities gradually weaken. This disorder, a motor neuropathy syndrome, is sometimes mistaken for amyotrophic lateral sclerosis (ALS) because of the similarity in the clinical picture, especially if muscle fasciculations are present. MMN is usually asymmetric and is thought to be autoimmune.

Multiple sclerosis (MS): A slowly progressive CNS disease characterized by disseminated patches of demyelination in the brain and spinal cord, resulting in multiple and varied neurological symptoms and signs, usually with remissions and exacerbation. The cause of MS is unknown but an immunological abnormality is suspected. An increased family incidence suggests genetic susceptibility, and women are somewhat more often affected than men. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and minor remission. Primary-progressive multiple sclerosis (PPMS) presents initially in the progressive form. A clinically isolated syndrome is the first neurologic episode, which is caused by inflammation/demyelination at one or more sites in the CNS. Progressive-relapsing multiple sclerosis (PRMS) is a rare form of MS (~5%) characterized by a steadily worsening disease state from onset, with acute relapses but no remissions.

Myelin: A lipid substance forming a sheath (known as the myelin sheath) around the axons of certain nerve fibers. Myelin is an electrical insulator that serves to speed the conduction of nerve impulses in nerve fibers. "Myelination" (also "myelinization") refers to the development or formation of a myelin sheath around a nerve fiber. Similarly, "remyelination" (also, "remyelinization") refers to the repair or reformation of the myelin sheath, such as following injury, exposure to a toxic agent, or an inflammatory response, or during the course of a demyelinating disease.

Neurodegenerative disease: Refers to any type of disease that is characterized by the progressive deterioration of the nervous system.

Neuropathy: A functional disturbance or pathological change in the peripheral nervous system. Axonal neuropathy refers to a disorder disrupting the normal functioning of the axons.

Paraproteinemic demyelinating polyneuropathy: A type of peripheral neuropathy characterized by auto antibodies directed against myelin associated glycoproteins (MAG). Anti-MAG antibodies inhibit the production of myelin, thereby leading to neuropathy.

Pelizaeus-Merzbacher disease (PMD): A rare central nervous system disorder in which coordination, motor abilities, and intellectual function are delayed to variable extents. The disease is one in a group of genetic disorders collectively known as leukodystrophies.

Peroneal muscular atrophy (PMA): A genetically and clinically heterogeneous group of inherited disorders of the peripheral nervous system characterized by progressive loss of muscle tissue and touch sensation across various parts of the body. This disease is also known as Charcot-Marie-Tooth disease (CMT), Charcot-Marie-Tooth neuropathy and hereditary motor and sensory neuropathy (HMSN).

Pharmaceutical composition: A composition containing one or more of the compounds described herein, or a pharmaceutically acceptable salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

Pharmaceutically acceptable carrier: Any ingredient other than the disclosed compounds, or a pharmaceutically acceptable salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

Pharmaceutically acceptable salt: Salts prepared by conventional methods. These include basic salts of inorganic and organic acids, such as, without limitation, hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, and mandelic acid. "Pharmaceutically acceptable salts" of the presently disclosed compounds also include those formed from cations such as, without limitation, sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reaction of the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms of the disclosed compounds. Descriptions of exemplary pharmaceutically acceptable salts can be found in Stahl and Wermuth, Eds., *Handbook of Pharmaceutical Salts; Properties, Selection and Use*, Wiley VCH (2008). When the compounds disclosed herein include an acidic group such as a carboxy group, then suitable pharmaceutically acceptable cation pairs for the carboxy group are well known to those skilled in the art and include, without limitation, alkaline, alkaline earth, ammonium, and quaternary ammonium cations. Such salts are known to those of skill in the art. Similarly when the compounds disclosed herein include a basic group such as an amino group, then suitable pharmaceutically acceptable anion pairs for the basic group are similarly well known and include halide, hydroxide, perhalate, halite, hypohalite, sulfate, sulfite, phosphate, phosphite, nitrate, nitrite, and others known to those of skill in the art. For additional examples of pharmacologically acceptable salts, see Berge et al, *J. Pharm. Sci.* 66, 1 (1977).

Progressive multifocal leukoencephalopathy (PML): A rare and usually fatal viral disease that is characterized by progressive damage or inflammation of the white matter of the brain in multiple locations. PML occurs almost exclusively in people with severe immune deficiency. The cause of PML is a type of polyomavirus called the JC virus. The virus is widespread, with 86% of the general population presenting antibodies, but it usually remains latent, causing disease only when the immune system has been severely weakened. PML is a demyelinating disease, in which the myelin sheath covering the axons of nerve cells is gradually destroyed, impairing the transmission of nerve impulses. The disease may occur in subjects (e.g., humans) with severe immune deficiency, such as transplant patients on immunosuppressive medications or those receiving certain kinds of medications. For example, PML has been associated with administration of rituximab (off-label use in the treatment of multiple sclerosis). It affects the white matter, which is mostly composed of axons from the outermost parts of the brain (cortex). Symptoms include weakness or paralysis, vision loss, impaired speech, and cognitive deterioration.

Sobetirome: A synthetic diarylmethane derivative that was investigated clinically as a potential therapeutic for hypercholesterolemia (see U.S. Pat. No. 5,883,294, which is incorporated by reference herein). Other names for sobetirome found in the literature and regulatory filings include QRX-431 and GC-1. Sobetirome is also referred to herein as compound 1.

Subject: An animal (e.g., a mammal, such as a human). A subject to be treated according to the methods described herein may be one who has been diagnosed with a neurodegenerative disease involving demyelination, insufficient myelination, or underdevelopment of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

Transverse myelitis: A neurological disorder caused by an inflammatory process of the grey and white matter of the spinal cord, leading to axonal demyelination. Demyelination arises idiopathically following infections or vaccination, or due to multiple sclerosis. Symptoms include weakness and numbness of the limbs as well as motor, sensory, and sphincter deficits. Severe back pain may occur in some patients at the onset of the disease.

Treatment: an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

Tropical spastic paraparesis (TSP): An infection of the spinal cord by human T-lymphotropic virus resulting in paraparesis, weakness of the legs. TSP is also known as HTLV associated myelopathy or chronic progressive myelopathy. As the name suggests, this disease is most common in tropical regions, including the Caribbean and Africa.

Van der Knaap disease: A form of hereditary CNS demyelinating disease. This disease is a type of leukodystrophy and is also known as megalencephalic leukoencephalopathy with subcortical cysts (MLC).

X-linked adrenoleukodystrophy (X-ALD, ALD, or X-linked ALD): A rare, inherited metabolic disorder that leads to progressive brain damage, mental deterioration, failure of the adrenal glands, muscle spasms, blindness and eventually death. ALD is one disease in a group of inherited disorders called leukodystrophies. Adrenoleukodystrophy progressively damages myelin. X-linked ALD male patients may be divided into 7 phenotypes: childhood cerebral (progressive neurodegenerative decline leading to a vegetative state), adolescent (similar to childhood cerebral form but with a slower progression), adrenomyeloneuropathy (progressive neuropathy, paraparesis, may progress to cerebral involvement), adult cerebral (dementia, similar progression to childhood cerebral form), olivo-ponto-cerebellar (cerebral and brain stem involvement), Addison disease (adrenal insufficiency), asymptomatic (no clinical presentation, subclinical adrenal insufficiency, or AMN phenotype). X-linked ALD female patients may be divided into 5 phenotypes: asymptomatic (no neurologic or adrenal involvement), mild myelopathy, moderate to severe myelopathy (similar to male AMN phenotype), cerebral (progressive dementia and decline), and adrenal (primary adrenal insufficiency). X-linked ALD patients may progress from one phenotype to another over the course of their life. ALD is also known as Addison-Schilder disease or Siemerling-Creutzfeldt disease.

Zellweger syndrome: A rare congenital disorder, characterized by the reduction or absence of functional peroxisomes in the cells of an individual. This disease is classified as a leukodystrophy and is one of three peroxisome biogenesis disorders that belong to the Zellweger spectrum of peroxisome biogenesis disorders.

Sobetirome Prodrugs

Disclosed compounds are of the formula:

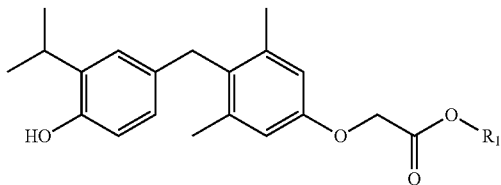

wherein $R_1$ is alkyl or aryl. This structure includes any pharmaceutically acceptable salts of the described structure. $R_1$ can be any alkyl or aryl including unsubstituted alkyl, substituted alkyl, heteroalkyl, substituted heteroalkyl, cycloalkyl, substituted cycloalkyl, heterocycloalkyl, substituted heterocycloalkyl, substituted aryl, heteroaryl, or substituted heteroaryl. In more particular examples, $R_1$ is ethyl, ethyltrimethylamino, ethylmorpholinyl, lysinyl, valinyl, phenylalaninyl, or glucosyl.

In other particular examples, $R_1$ is alkylamino. In these examples, $R_1$ can be substituted alkylamino, cycloalkylamino, or substituted cycloalkylamino. Examples of these compounds can have the structure:

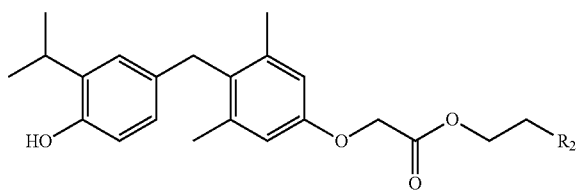

wherein $R_2$ is amino or alkylamino. In more particular examples, the structure is

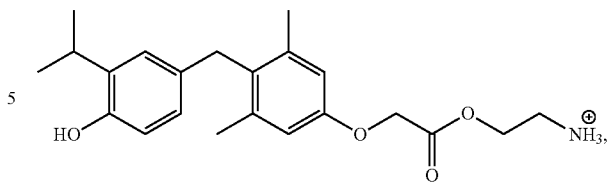

including any pharmaceutically acceptable salt thereof, such as a halide salt.

In still more particular examples, the structure is:

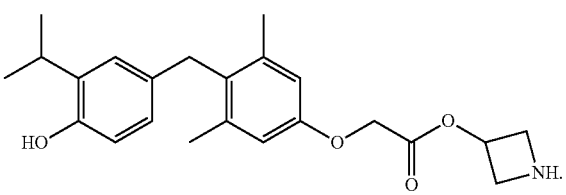 [SMILES: Cc1cc(OCC(=O)OC2CNC2)cc(C)c1Cc1ccc(O)c(C(C)C)c1]

Although systemically administered sobetirome distributes predominantly to the liver, there is indirect evidence from several prior studies indicating that sobetirome does distribute to the CNS in a potentially useful capacity (Takahashi N et al, *Biol Pharm Bull* 37, 1103-1108 (2014); Trost S et al, *Endocrinology* 141, 3057-3064 (2000), Bernal J, *Nat Clin Pract Endrcrinol Metab* 3, 249-259 (2007); Oppenheimer J H and Schwartz H L, *Endocr Rev* 18, 462-475 (1997); and Bernal J, *J Endocrinol Invest* 25, 268-288 (2002); all of which are incorporated by reference herein). However, quantitative data disclosed herein reveals that the brain/serum ratio of sobetirome is 0.2 (Table 2, below), a value that is slightly below the optimum range of 0.3-1.0 for CNS drugs (Doran A et al, *Drug Metab Sispos* 33, 165-174 (2005) and Reichel A, *Curr Drug Metab* 7, 183-203 (2006); both of which are incorporated by reference herein).

Disclosed herein are esters of sobetirome with improved blood brain barrier (BBB) permeability. These structures are alcohols designed to increase the BBB permeability of the sobetirome ester. Selected alcohols included groups that were though to either enhance passive diffusion across the BBB or facilitate active transport by BBB transporters.

Structures thought to utilize both active and passive transport mechanisms were examined. Passive transport prodrugs include a simple alkyl alcohol (compound 7), amino-alcohols (compounds 9, 11, and 15) and amino-acids (compound 14). Active transport based prodrug esters were designed to take advantage the presence of LAT transporters, amino-acid transporters, glucose transporters, or choline transporters found at the BBB (Lee G et al, Pharmacol Rev 53, 569-596 (2001); incorporated by reference herein).

Compounds 7-18

The synthesis of the sobetirome prodrugs was achieved in 5 linear steps starting from 2-isopropylphenol and 2,6-dimethyl-4-hydroxybenzaldehyde. The major step joining the phenolic and carboxylate ends of sobetirome was accomplished using an aryl Grignard prepared according to Knochel's procedure (Boymond L et al, *Agnew Chem Int Ed* 37, 1701-1703 (1998); incorporated by reference herein). The inner ring carbxylate (compound 3) intermediate was synthesized by alkyalting 2,6-dimethyl-4-hydroxybenzaldehyde (compound 2) with tert-butyl chloroacetate in a high yield. The phenolic portion of sobetirome (compound 1) was prepared by first iodinating 2-isopropylphenol (compound 4) at the para position using NaI and NaOCl (Edgar K J and Falling S N, *J Organ Chem* 55, 5287-5291 (1990), incorporated by reference herein). The phenol was then alkylated with benzyl bromide resulting in the benzyl protected phenol (compound 5). The inner-ring carboxylate portion of sobetirome (compound 1) was synthesized by alkylating 2,6-dimethyl-4-hydroxybenzaldehyde with 2-chloro-t-butylacetate resulting in (compound 5). The coupling of compound 5 and compound 3 was synthesized by first generating the aryl Grignard reagent of compound 5 via the Knochel procedure (Boymond L et al, 1998 supra) with iPrMgCl. The aryl Grignard reagent was then cooled to −78° C. and a solution of compound 3 in THF was added. This resulted in the corresponding coupled product containing a carbinol in the methylene bridge connecting the two fragments. The carbinol and t-butyl ester were then removed via the actions of TFA and triethylsilane (Penning T D et al, *J Med Chem* 43, 721-735 (2000); incorporated by reference herein) resulting in the key intermediate compound 6 in gram quantities and a 55% overall yield for the two steps (Scheme 1)

72, 6599-6601 (2007); incorporated by reference herein). The choline prodrug (compound 8) was next synthesized. After a few unsuccessful attempts at esterification of compound 6 with choline chloride and the acid chloride of compound 6, an alkylation of compound 6 with (2-Bromoethyl) trimethylammonium bromide and K₂CO₃ was attempted (Smith N D et al, *Bioorg Med Chem Lett* 15, 3197-3200 (2005); incorporated by reference herein). This resulted in the generation of the corresponding benzyl-protected ester which was then deprotected with the same 10% Pd/C and triethylsilane conditions giving the choline-sobetirome prodrug (compound 8) in 39% overall yield. The 4-(2-hydroxyethyl)morpholine sobetirome prodrug (compound 9) was synthesized by treating a cooled solution of 4-(2-hydroxyethyl)morpholine, DMAP, and DCM with a solution of the acid chloride (compound 6a) and DCM. Following the same benzyl deprotection method, this resulted in the morpholino prodrug (compound 9) in a 48% yield. (Scheme 2).

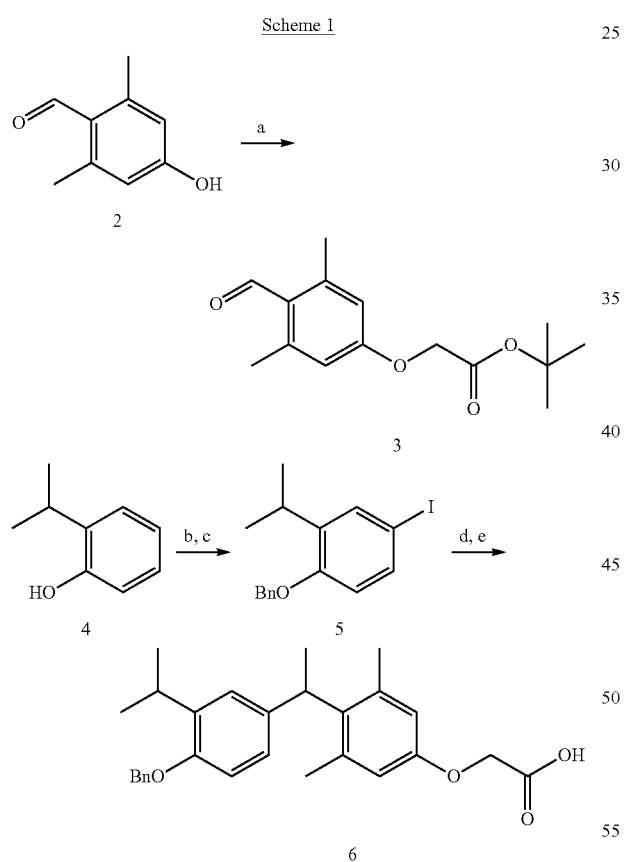

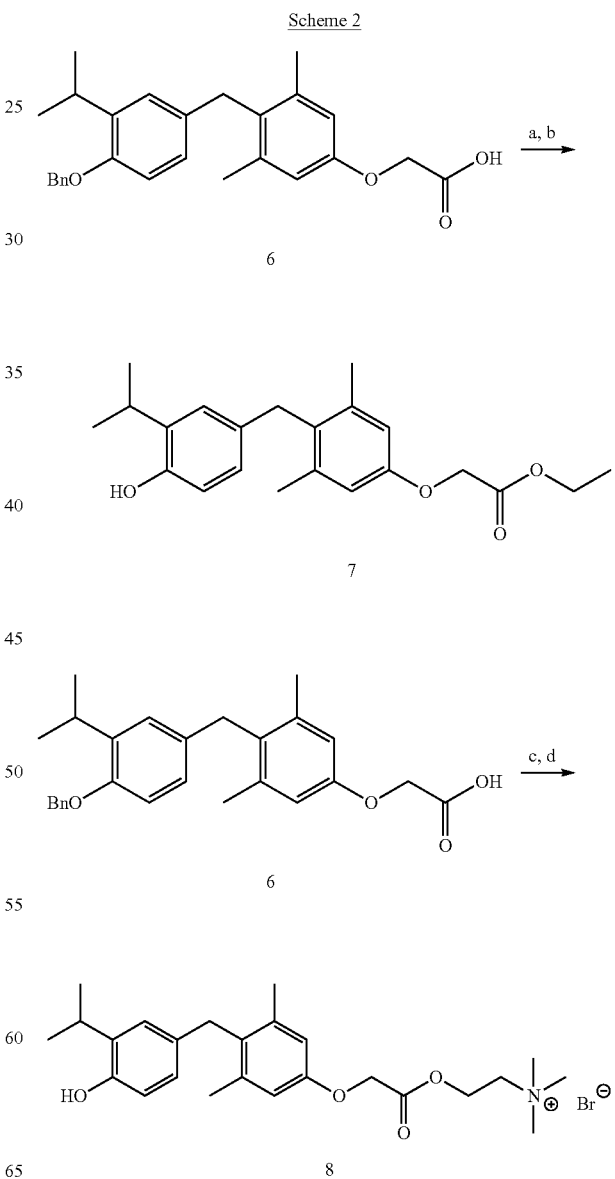

Scheme 1: Synthesis of benzyl-protected Sobetirome compound 6. Reagents and Conditions: (a) DMF, Cs₂CO₃, t-butyl chloroacetate, 89%; (b) NaI, NaOCl, NaOH, H₂O, 75%; (c) K₂CO₃, benzyl bromide, DMF, 75° C., 77%; (d) (i) iPrMgCl, THF, 4° C. MS, (ii) 3, THF, -78° C.; (e) DCM, Et₃SiH, TFA, 55% (two steps).

With the phenol-protected sobetirome (compound 6) in hand, the first prodrug synthesized was the ethyl ester version of sobetirome. The ethyl ester (compound 7) was synthesized by treating compound 6 with HCl (ethanol) and then deprotecting the benzyl ether with 10% Pd/C and triethylsilane (Mandal P K and McMurray J S, *J Org Chem*

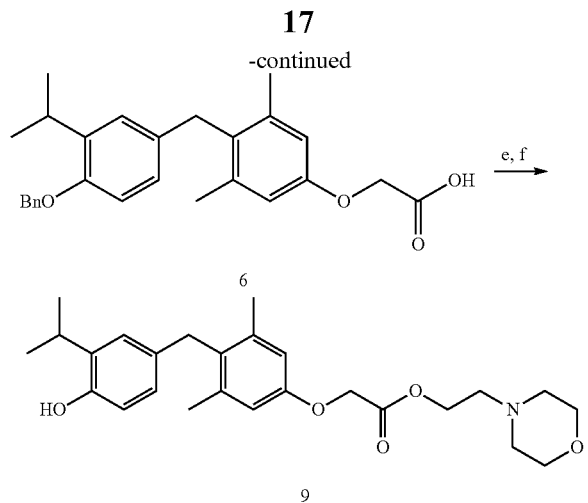

Scheme 2. Synthesis of Sobetirome-prodrugs 7, 8 and 9. Reagents and Conditions: (a) 1M HCl (ethanol); (b) 10% Pd/C, Et$_3$SiH, MeOH, 62% (two steps); (c) K$_2$CO$_3$, DMF, (2-Bromoethyl) trimethylammonium bromide; (d) 10% Pd/C, Et$_3$SiH, MeOH, 39% (two steps); (e) (i) oxalyl chloride, DCM, DMF, (ii) 4-(2-hydroxyethyl)morpholine, DMAP, DCM; (f) 10% Pd/C, Et$_3$SiH, MeOH, 48% (two steps)

The next set of sobetirome prodrugs synthesized contained an ethanolamine sidechain for increasing the log P and adding a positive charge to sobetirome or for acting as a linker to amino acids. The ethanolamine sobetirome prodrug synthesis was started in a similar manner to that of compound 9 except boc-ethanolamine was used. The protected ethanolamine intermediate (compound 10) was then subjected to benzyl deprotection conditions, followed by HCl (ethyl acetate) to remove the boc residue resulting in (compound 11) in a 37% overall yield for the three steps. The lysine and valine sobetirome prodrugs were synthesized by first deprotecting the boc residue of compound 10 resulting in the free primary amine (compound 12). The primary amine of compound 12 was then coupled with the carboxylic acid of Boc-Lysine(Boc)-OH and Boc-Valine using EDCl, HoBt, DIEA and DMF. (Scheme 3).

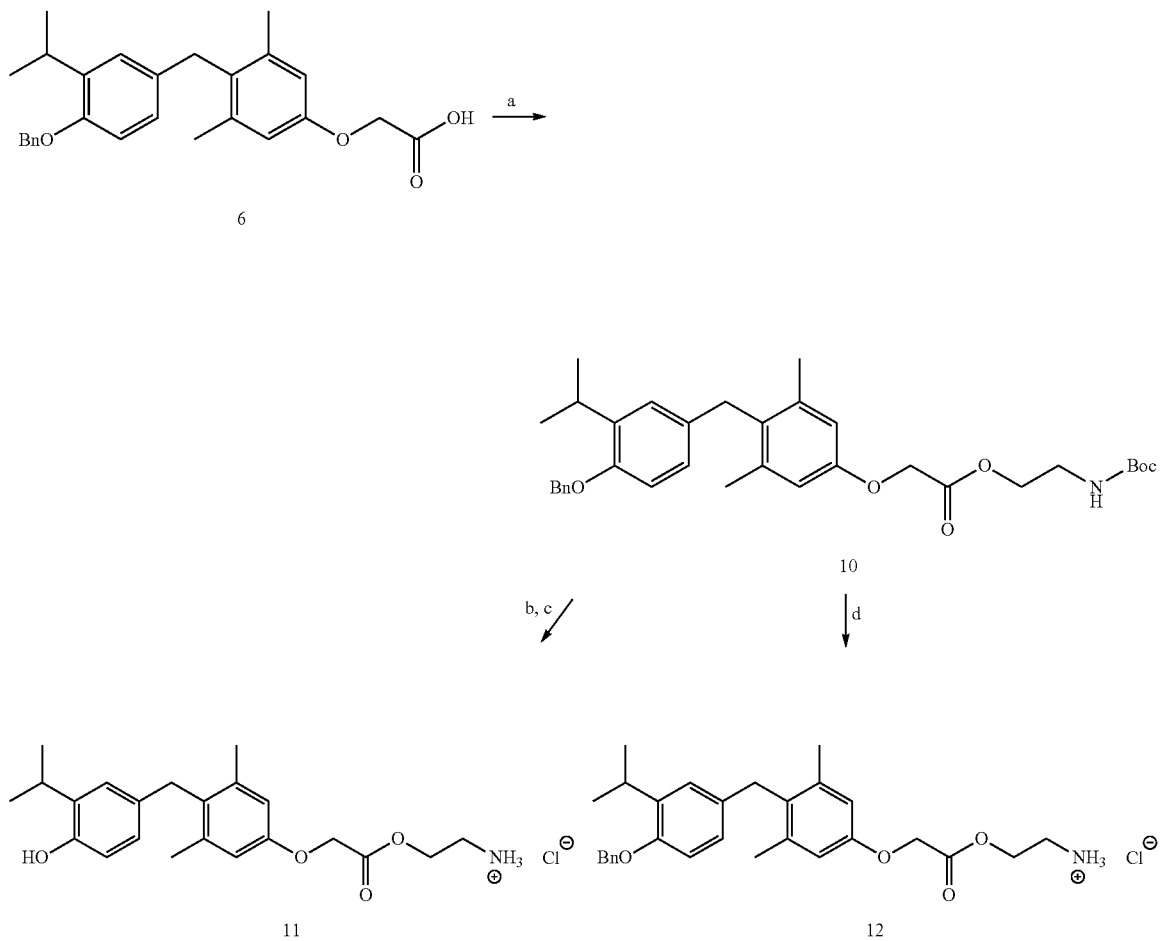

Scheme 3: Synthesis of Sobetirome-prodrug 11 and intermediate 12. Reagents and Conditions: (a) i) oxalyl chloride, DCM, DMF, (ii) N-Boc-ethanolamine, DMAP, DCM, 72%; (b) 10% Pd/C, Et$_3$SiH, MeOH; (c) 1M HCl (ethyl acette), 51%. (d) 1M HCl (ethyl acetate), 81%.

Following the standard benzyl ether deprotection and boc deprotection conditions yielded the Sobetirome-Lysine (compound 13) and Sobetirome-Valine (compound 14) (Scheme 4) Lastly, the azetidine-sobetirome prodrug was designed and synthesized in an effort to examine the effect on BBB permeability of a prodrug with a secondary alcohol versus a primary alcohol (compound 11). Following a similar synthetic sequence as was used with compound 11, the Sobetirome-Azetidine was synthesized in a 35% yield over the three steps (Scheme 5).

Scheme 5

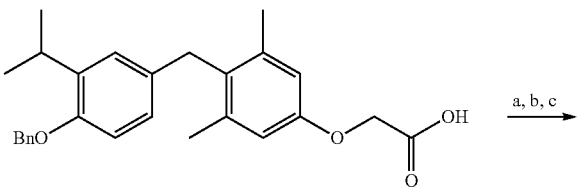

Scheme 4

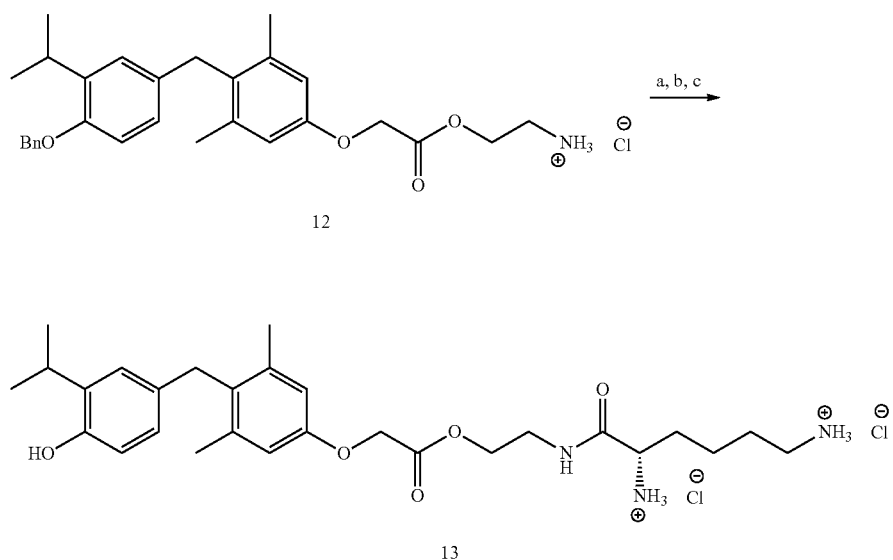

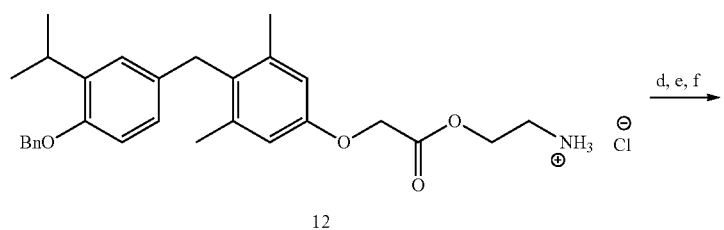

Scheme 4. Synthesis of Sobetirome-prodrugs 13 and 14. Reagents and Conditions: (a) Boc-Lys(Boc)-OH, EDCl-HCl, HobT-H₂O, DMF, DIEA; (b) 10% Pd/C, Et₃SiH, MeOH; (c) 1M HCl (ethyl acetate), 40% (d) Boc-Valine-OH, EDCl-HCl, HoBt-H₂O, DMF, DIEA; (e) 10% Pd/C, Et₃SiH, MeOH; (f) 1M HCl (ethyl acetate), 32%.

-continued

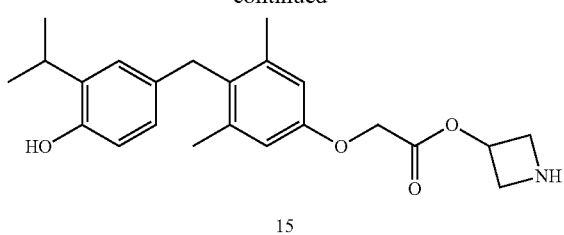

15

Scheme 5. Synthesis of Sobetirome-prodrug15.
Reagents and Conditions: (a) i) oxalyl chloride, DCM DMF,
(ii) 1-(tert-butylcarbonyl)-3-hydroxyazetidine, DMAP, DCM,;
(b) 10% Pd/C, Et$_3$SiH, MeOH, 51% (two steps);
(c) 1M HCl (ethyl acetate), 45% (three steps).

Additional Sobetirome-based prodrugs were all designed to utilize active transport mechanisms to gain access to the CNS. The Sobetirome-Tyrosine prodrug was synthesized using Schotten-Baumann conditions as described by Millar and Hare[14]. The acid chloride of compound 6 was slowly added to a mixture of boc-tyrosine, NaOH, acetone and water cooled to 0° C. The resulting phenolic ester was then subjected to benzyl ether and boc deprotection conditions yielding compound 16. The Sobetirome-Glucose prodrug was prepared by first synthesizing benzyl 2,3,4-tri-O-benzyl-beta-D-glucopyranoside (compound 17) as described in Lu W et al, *Carbohydr Res* 340, 1213-1217 (2005); incorporated by reference herein. The ester was formed by cooling a solution of compound 17, DMAP, and DCM to 0° C. and slowly adding the acid chloride generated from compound 6. With the ester in hand, the five benzyl ethers were deprotected using 100 mol % of 10% Pd/C and 60 equiv of triethylsilane yielding compound 18 in a 44% overall yield.

-continued

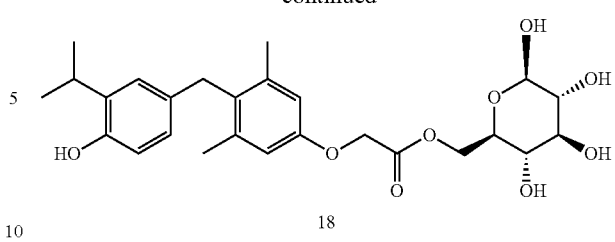

18

Scheme 6. Synthesis of Sobetirome-prodrug16 and 18.
Reagents and Conditions: (a) i) oxalyl chloride, DCM DMF,
(ii) N-t-Boc-L-Tyrosine, NaOH, Acetone;
(b) 10% Pd/C, Et$_3$SiH, MeOH, 51% (two steps);
(c) 1M HCl (ethyl acetate), 12.5% (three steps);
(d) i) oxalyl chloride, DCM DMF, (ii) 17, DMAP, DCM;
(e) 10% Pd/C, Et$_3$SiH, Acetic Acid, THF, 44% (two steps).

Compounds 19-32

Following the biological testing of the first-generation prodrugs a second set of prodrugs was prepared that was primarily focused around the ethanolamine pro-moiety (compounds 19-32). The second-generation Sobetirome-based prodrugs were synthesized using the same methodology described above except that Cbz-protected amino alcohols were used for some of the amino-alcohols instead of the standard boc-protected amino alcohols. The use of the cbz-protecting group allowed us to perform one deprotection (10% Pd/C, Et$_3$SiH) to remove both the benzyl and cbz protecting groups. This resulted in a more stream-lined synthesis and also avoided the troublesome acidic deprotection of the boc residue for some of the more acid-sensitive prodrugs. Using the synthetic route depicted in Scheme 7, additional Sobetirome-prodrugs were synthesized.

Scheme 6

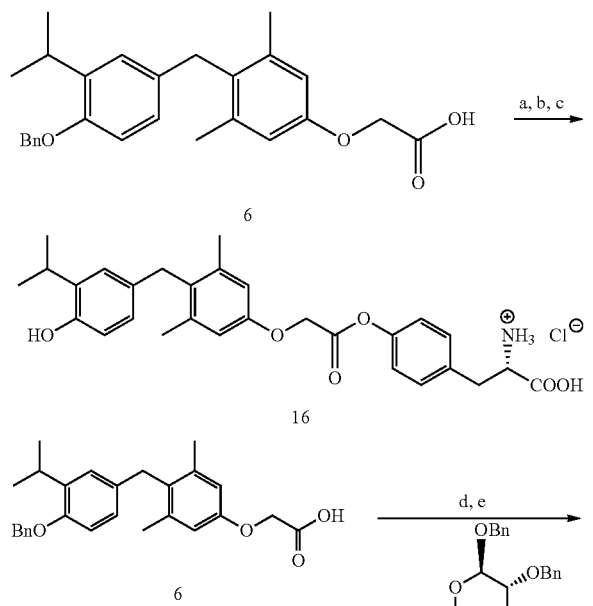

Scheme 7

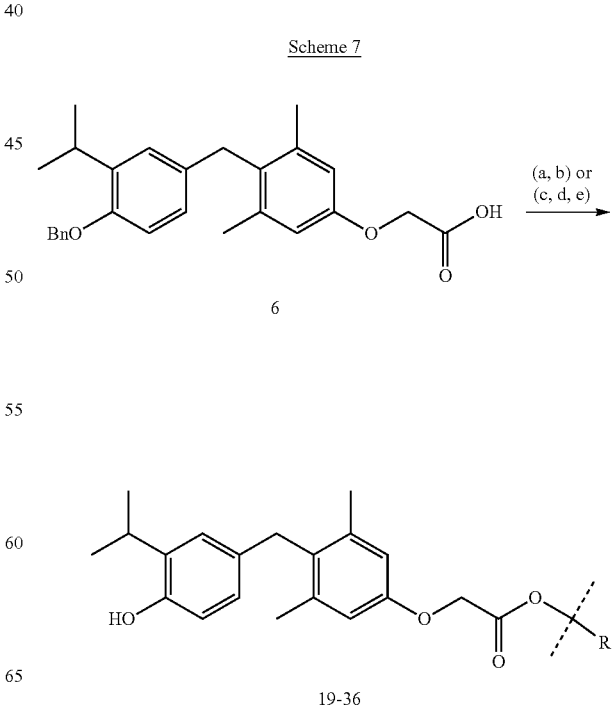

R =

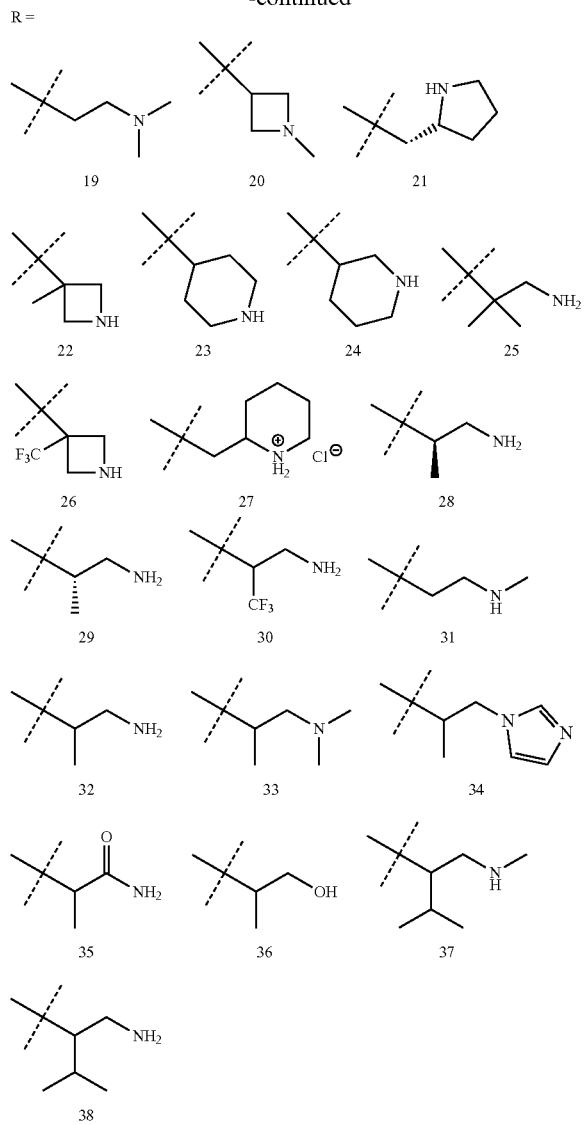

Scheme 7: Reagents and Conditions: (a) i) oxalyl chloride, DCM DMF,
(ii) alcohol or N-Cbz-amino alcohol, DMAP or TEA/DMAP, DCM or THF;
(b) 10% Pd/C, Et₃SiH, MeOH;
(c) i) oxalyl chloride, DCM, DMF (ii) N-Boc-amino alcohol, DMAP, DCM or THF
(d) 10% Pd/C, Et₃SiH, MeOH, THF;
(e) 1M HCl (ethyl acetate).

Biology

Figure 1B:
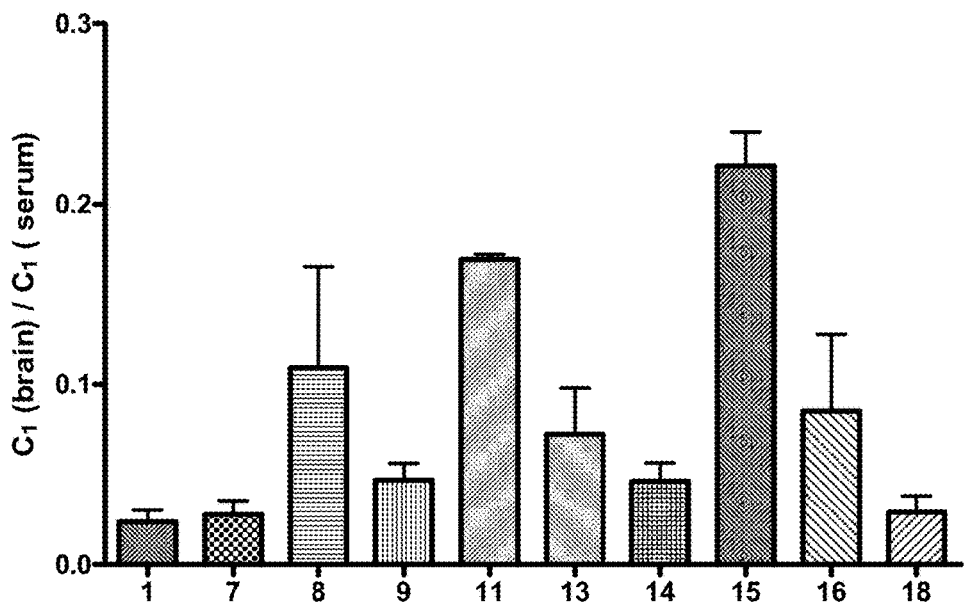
FIG. 1B is a bar graph depicting (brain/serum) ratios of the indicated compounds following intraperitoneal administration of sobetirome (compound 1) (1.5 μmol/kg) or prodrugs 7, 8, 9, 11, 13, 14, 15, 16, 18 (1.5 μmol/kg) in mice.
Figure 1C:
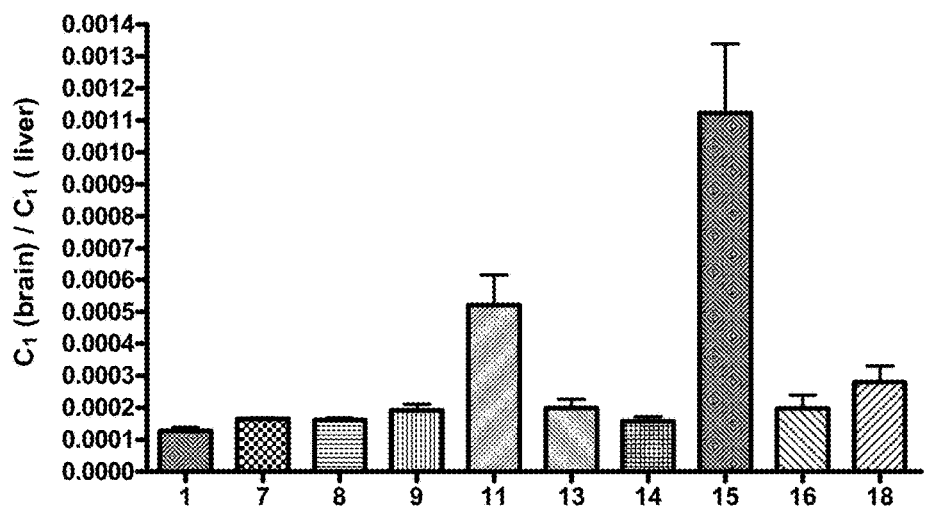
FIG. 1C is a bar graph depicting (brain/liver) ratios of the indicated compounds following intraperitoneal administration of Sobetirome (compound 1) (1.5 μmol/kg) or prodrugs 7, 8, 9, 11, 13, 14, 15, 16, 18 (1.5 μmol/kg) in mice.

A biodistribution study in mice was performed on each prodrug to determine the brain, liver, and serum levels of sobetirome following a systemic (intraperitoneal) administration. The mice received an equimolar dose (1.5 µmol/kg) of prodrug and one cohort received the same dose of sobetirome as a control. Tissue and blood were collected 30 minutes post-injection and the concentration of sobetirome was determined using an LC-MS/MS. Most of the prodrugs tested in this way did not show increased brain sobetirome levels compared to the equimolar systemic injection of sobetirome (FIG. 1A). However, significant brain sobetirome level increases were observed with prodrugs 11 and 15, which are both sobetirome esters of ethanolamines. In addition to increased brain sobetirome levels, these two esters showed significantly lower liver and serum sobetirome levels compared to the direct sobetirome injection leading to 7- and 9-fold increases compared to sobetirome in the brain/serum sobetirome ratio for prodrugs 11 and 15, respectively (FIG. 1B). The brain/liver sobetirome ratio was increased compared to sobetirome injection by 5- and 10-fold for 11 and 15, respectively (FIG. 1C)

Figure 2A:
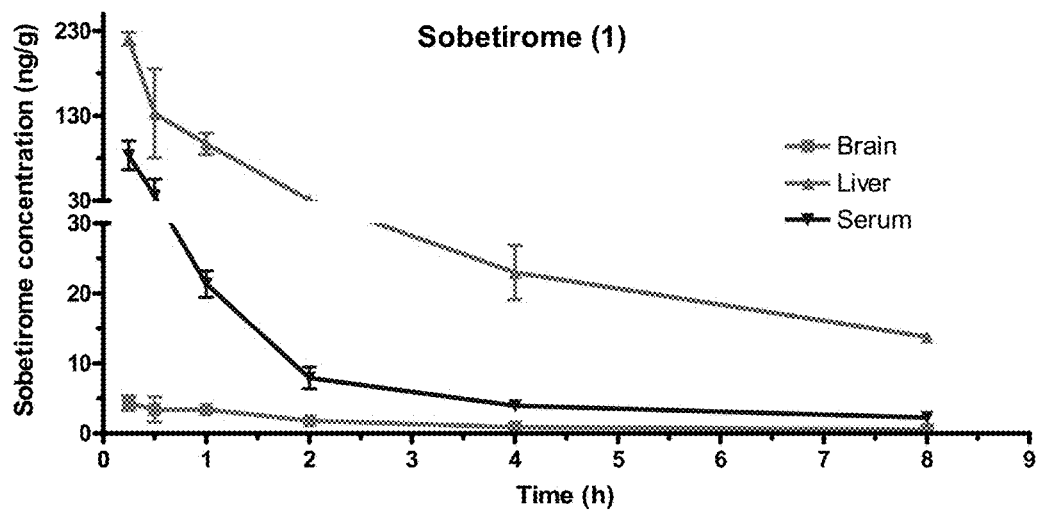
FIG. 2A is a plot of the concentrations in the brain, liver, and serum (ng/g) at the indicated time post intraperitoneal administration of sobetirome (compound 1) (1.5 μmol/kg).
Figure 2B:
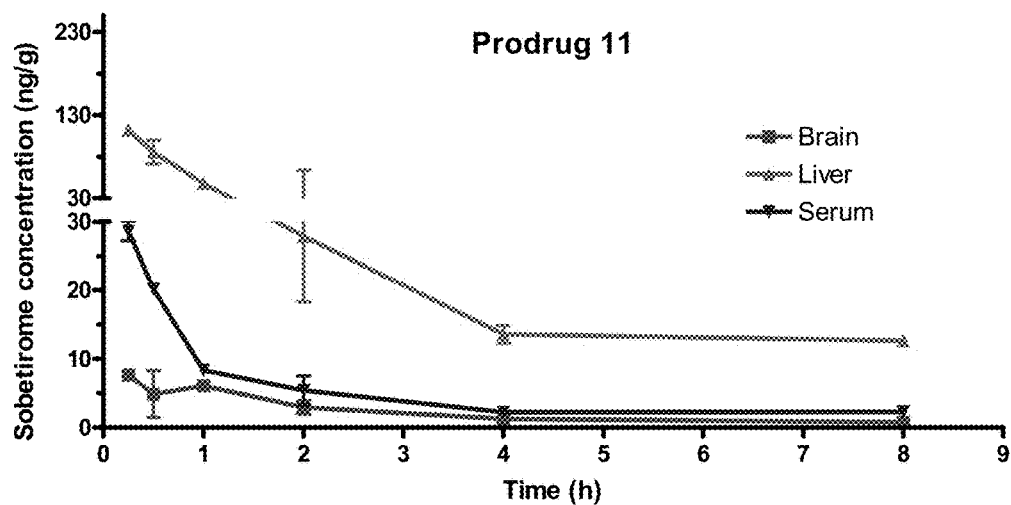
FIG. 2B is a plot of the concentrations in the brain, liver, and serum (ng/g) at the indicated time post intraperitoneal administration of prodrug 11 (1.5 μmol/kg).
Figure 2C:
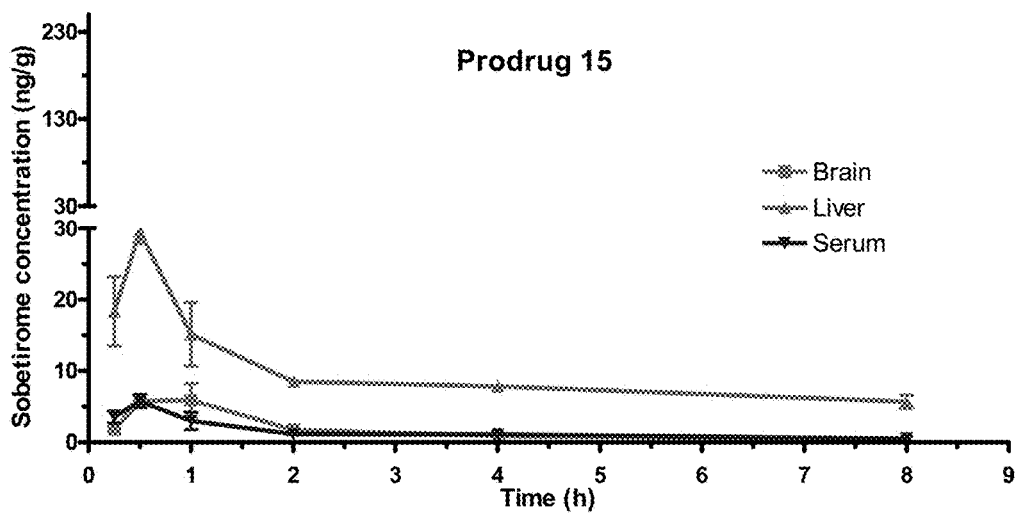
FIG. 2C is a plot of the concentrations in the brain, liver, and serum (ng/g) at the indicated time post intraperitoneal administration of prodrug 15 (1.5 μmol/kg).

The single time point pilot study was followed up for 11 and 15 vs. sobetirome with an 8-hour time course distribution study in mice. A pharmacokinetic study showed that the $t_{1/2}$ of sobetirome in mice is 1.5 hours indicating that an 8 hour study would be sufficient to quantify >95% of the sobetirome exposure. The sobetirome AUC, $C_{max}$, and $T_{max}$ values in brain, liver and serum resulting from systemic administration of sobetirome, prodrug 11, and prodrug 15 are shown in Table 1 and the curves used to obtain these values are shown in FIGS. 2A, 2B and 2C.

TABLE 1

Pharmacokinetic parameters ($AUC_{0 \to t}$ and $T_{max}$) of sobetirome in mouse serum, brain, and liver tissues after administration of sobetirome (1) (1.5 µmol/kg) or prodrugs 11 and 15 (1.5 umol/kg).

| | Sobetirome (1) | | prodrug 11 | | prodrug 15 | |
|---|---|---|---|---|---|---|
| Tissue | $AUC_{0 \to t}$ (ng/g*h) | $T_{max}$ (min) | $AUC_{0 \to t}$ (ng/g*h) | $T_{max}$ (min) | $AUC_{0 \to t}$ (ng/g*h) | $T_{max}$ (min) |
| Serum | 68.2 | <15 | 36.8 | <15 | 10.9 | 30 |
| Brain | 10.8 | <15 | 17.1 | <15 | 14.3 | 60 |
| Liver | 293 | <15 | 190 | <15 | 72.4 | 30 |

Figure 2D:
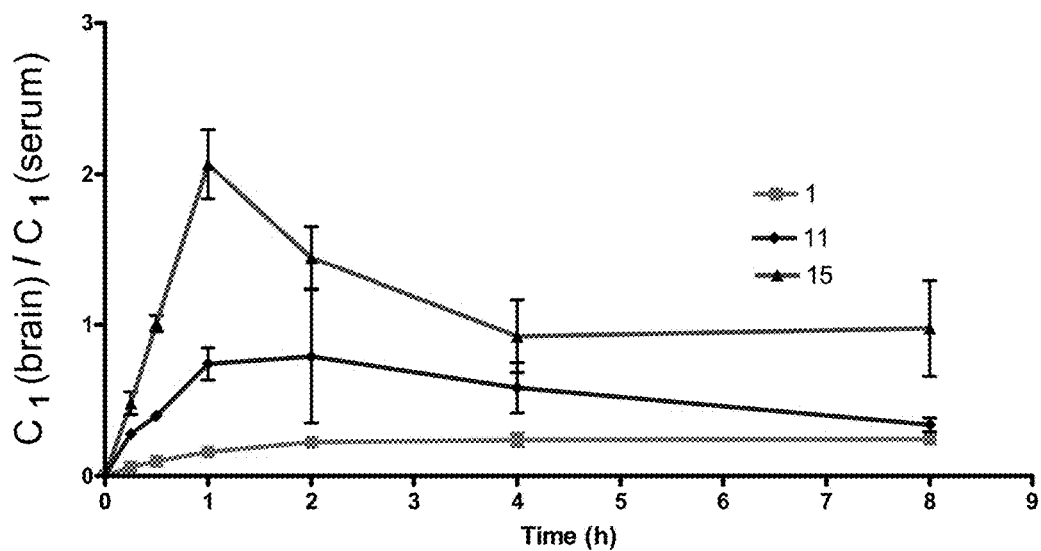
FIG. 2D is a plot of the brain/serum ratios of sobetirome (compound 1) or prodrug 11 or prodrug 15 at the indicated time post intraperitoneal administration (1.5 μmol/kg).
Figure 3A:
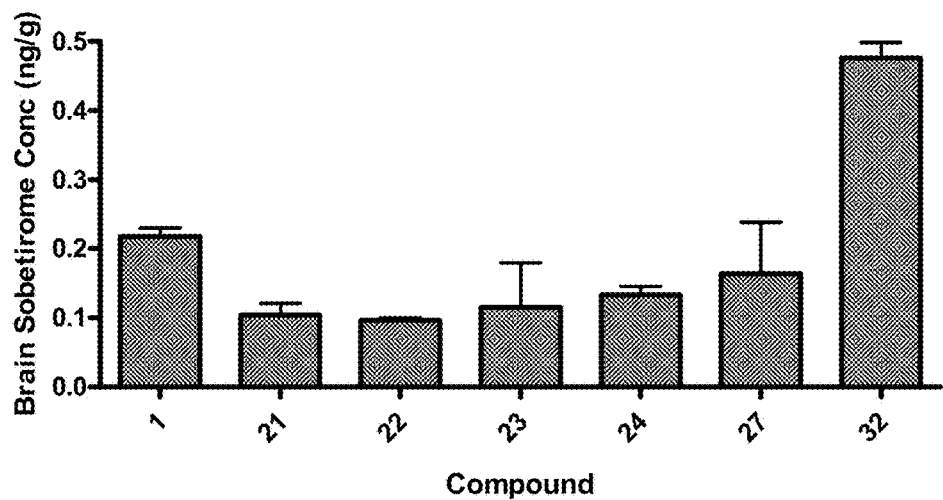
FIG. 3A is a bar graph depicting the concentration of the indicated compounds in brain (ng/g of tissue) following intraperitoneal administration (1.5 μmol/kg).
Figure 3B:
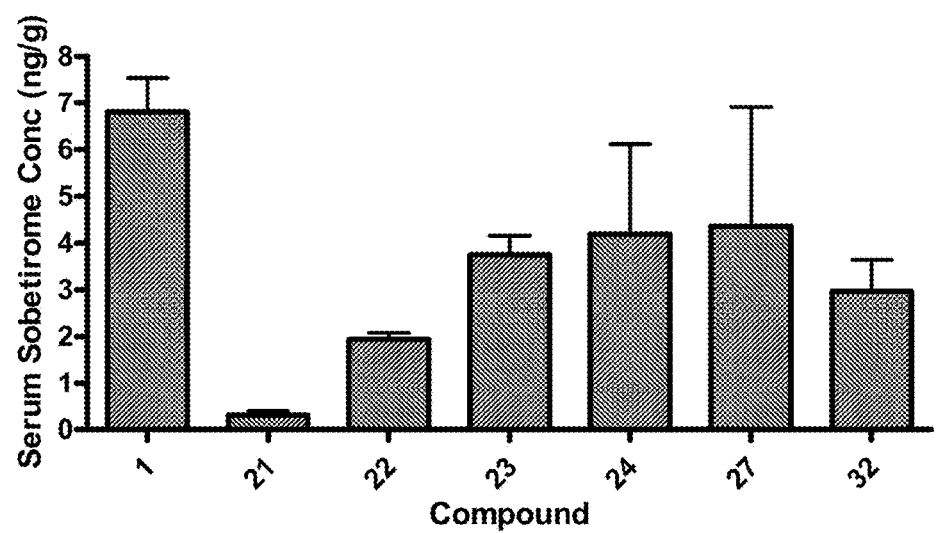
FIG. 3B is a bar graph depicting the concentration of the indicated compounds in serum (ng/g of tissue) following intraperitoneal administration (1.5 μmol/kg).

The results show that the trend observed in the single time point study is observed in the full time course also; prodrugs 11 and 15 generate increased sobetirome exposure (compared to direct sobetirome injection) in brain and decreased sobetirome exposure in liver and serum. The brain/serum ratio based on AUC was found to be 0.16 for sobetirome injection compared to 0.46 and 1.31 for 11 and 15, respectively (Table 2). Clear $C_{max}$ and $T_{max}$ values were obtained only for prodrug 15 (Table 1) as maximal sobetirome concentrations were recorded at the initial (15 min) time points in brain, liver, and serum for both sobetirome and 11. In addition to improved sobetirome brain/serum ratios, prodrug 15 also displayed a five-fold increase in sobetirome $AUC_{(brain)}/AUC_{(liver)}$ relative to sobetirome (Table 2 and FIG. 2D).

TABLE 2

Sobetirome tissue distribution values ($AUC_{brain}/AUC_{serum}$) and ($AUC_{brain}/AUC_{liver}$) after ip administration of sobetirome or prodrugs 11 and 15.

| | Sobetirome Distribution | |
|---|---|---|
| Compound | $AUC_{brain}/AUC_{serum}$ | $AUC_{brain}/AUC_{liver}$ |
| 1 | 0.2 | 0.037 |
| 11 | 0.5 | 0.090 |
| 15 | 1.3 | 0.20 |

It is not clear why the disclosed prodrugs other than prodrugs 11 and 15 did not improve sobetirome CNS distribution, even though each of these seven esters had literature precedent for improving CNS distribution of other carboxylic acid containing drugs. That prodrugs 11 and 15 were the only two from the series that improved CNS distribution suggests that the ethanolamino ester is particularly well suited for this role at least with respect to sobetirome and related carboxylic acid containing drugs. The superior CNS distribution properties of 15 compared to 11 suggests that either a secondary amine or $C_1$ branching is beneficial with respect to CNS uptake, circulating ester half-life, or both. The 2-morpholinoethyl ester 9 that contains a tertiary ethanolamine did not significantly increase sobetirome brain levels (FIG. 1A) or the brain/serum ratio suggesting that the more highly substituted tertiary ethanolamine is not tolerated. Likewise, the structurally related quaternary ammonium choline ester 8 did not improve CNS distribution of sobetirome despite reports of its successful use in promoting CNS distribution of a carboxylate containing COX inhibitor (Smith N D et al, *Bioorg Med Chem Lett* 15, 3197-3200 (2005), incorporated by reference herein). This suggests the requirement for an amino group that can shuttle between neutral and cationic forms for the mechanism involved in the BBB transport of these sobetirome-aminoethyl ester prodrugs.

The structural characteristics of the sobetirome-azetidine prodrug (compound 15) that may contribute to its ability to increase brain concentration of sobetirome are the presence of the secondary alcohol ester linkage and the secondary amine. The branching found on the secondary alcohol ester is hypothesized to cause the delay in time to reach $C_{max}$ (1 hour) relative to sobetirome (compound 1) (15 min) (10). In addition, the secondary amine in prodrug 15 (clogP: 5.18) maintains a similar clogP as Sobetirome (clogP: 4.87) and at the same time eliminates the negative charge on Sobetirome found at physiological pH. The loss of the negative charge coupled with the slow release mechanism found in prodrug 15 makes this a unique prodrug capable of increasing the Sobetirome $AUC_{(brain)}/AUC_{(serum)}$ ratio to a value of 1.31.

Methods

Animal Studies: Experimental protocols were in compliance with the National Institutes of Health Guide for the Care and Use of Laboratory Animals and approved by the Oregon Health & Science University Institutional Animal Care & Use Committee. Wild type male C57Bl/6 mice, aged 8-10 weeks, were housed in a climate controlled room with a 12 hour light-dark cycle with ad libitum access to food and water. Mice were injected once intraperitoneally (IP) with sobetirome and prodrugs at 3.05 µmol/kg. Euthanasia was performed on three mice per time points at the following times (0.15 h, 0.5 h, 1 h, 2 h, 4 h, and 8 h) and the tissues and blood were harvested. Tissues were immediately frozen and blood was kept on ice for a minimum of 30 minutes and then spun down at 7,500×G for 15 minutes. Serum (100 uL) was collected and was stored with tissues at −80° C. until samples were processed.

Serum Processing: The serum samples were warmed to room temperature and 10 µL of 2.99 µM internal standard ($D_6$-Sobetirome) was added to them. Acetonitrile (500 µL) was added and the sample was vortexed for 20 seconds. The sample was then centrifuged at 10,000×G for 15 minutes at 4° C. Next, 90% of the upper supernatant was transferred to a glass test tube and concentrated using a speedvac for 1.5 hours at 45° C. The dried sample was then dissolved in 400 µL of 50:50 ACN:$H_2O$ and vortexed for 20 seconds. The resulting mixture was transferred to an Eppendorf and centrifuged at 10,000×G for 15 minutes. The supernatant was filtered with 0.22 µM centrifugal filters and submitted for LC-MS/MS analysis. The standard curve was made with 100 µL of serum from an 8-10 week old mouse not injected with Sobetirome or prodrug. The processing was performed exactly the same except after filtering the sample was split amongst 6 vials. To 5 out of the 6 vials was added Sobetirome to make final concentrations in matrix of (0.1 pg/µL, 1 pg/µL, 10 pg/µL, 100 pg/µL, and 1000 pg/µL).

Brain Processing: The brain samples were warmed to room temperature and transferred to a homogenizer tube with 5 GoldSpec ⅛ chrome steel balls (Applied Industrial Technologies). The resulting tube was weighed and then 1 mL of $H_2O$ was added, followed by 10 µL of 2.99 µM internal standard ($D_6$-sobetirome). The tube was then homogenized with a Bead Bug® for 30 seconds and then transferred to a Falcon tube containing 3 mL of ACN. ACN (1 mL) was used to wash homogenizer tube and the solution was transferred back to the Falcon tube. The sample was then processed using the same method for the serum processing except the sample was concentrated in a glass tube using a speedvac for 4 hours at 45° C.

Liver Processing: The liver samples were warmed to room temperature and transferred to a homogenizer tube with 5 GoldSpec ⅛ chrome steel balls (Applied Industrial Technologies). The resulting tube was weighed and then 1 mL of $H_2O$ was added, followed by 10 µL of 2.99 µM internal standard ($D_6$-Sobetirome). The tube was then homogenized with a Bead Bug for 30 seconds. A small sample (100 µL) was then taken from the homogenized mixture and processed. This was done because the liver levels found in some samples were too high for the LC-MS/MS instrument. The samples were then processed using the serum processing method.

General Chemistry: $^1$HNMR were taken on a Bruker 400®. All $^1$HNMR were calibrated to the NMR solvent reference peak ($D_6$-DMSO, $CDCl_3$, $CD_3OD$). High resolution mass spectrometry (HRMS) with electrospray ionization was performed by the Bioanalytical MS Facility at Portland State University. Inert atmosphere reactions were performed under argon gas passed through a small column of drierite and were conducted in flame-dried rbfs. Anhydrous tetrahydrofuran (THF), dichloromethane (DCM), and dimethylformamide (DMF) were obtained from a Seca Solvent System. All other solvents used were purchased from Sigma-Aldrich or Fisher. Purity analysis of final compounds was determined to be >95% by HPLC. HPLC analysis was performed on a Varian ProStar HPLC with an Agilent Eclipse Plus® C18 5 µM column (4.6×250 mm) with a gradient of 10% to 95% acetonitrile (0.1% TFA) over 15 minutes.

Pharmaceutical Compositions

The compounds disclosed herein may be included in pharmaceutical compositions (including therapeutic and prophylactic formulations), typically combined together with one or more pharmaceutically acceptable carriers (known equivalently as vehicles) and, optionally, other therapeutic ingredients.

Such pharmaceutical compositions can formulated for administration to subjects by a variety of mucosal administration modes, including by oral, rectal, intranasal, intrapulmonary, intravitrial, or transdermal delivery, or by topical delivery to other surfaces including the eye. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other examples, the compound can be administered ex vivo by direct exposure to cells, tissues or organs originating from a subject.

To formulate the pharmaceutical compositions, the compound can be combined with various pharmaceutically acceptable additives. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween®-80), solubility enhancing agents (for example, cyclodextrins and derivatives thereof), stabilizers (for example, serum albumin), and reducing agents (for example, glutathione) can be included.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7. The compound can be dispersed in any pharmaceutically acceptable carrier, which can include a hydrophilic compound having a capacity to disperse the compound, and any desired additives. The carrier can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a carrier, for example, polylactic acid, poly(lactic acid-glycolic acid) copolymer, polyhydroxybutyric acid, poly(hydroxybutyric acidglycolic acid) copolymer and mixtures thereof.

Alternatively or additionally, synthetic fatty acid esters such as polyglycerin fatty acid esters, sucrose fatty acid esters and the like can be employed as carriers. Hydrophilic polymers and other vehicles can be used alone or in combination, and enhanced structural integrity can be imparted to the vehicle by partial crystallization, ionic bonding, cross-linking and the like. The carrier can be provided in a variety of forms, including fluid or viscous solutions, gels, pastes, powders, microspheres, and films for direct application to a mucosal surface.

The compound can be combined with the carrier according to a variety of methods, and release of the compound can be by diffusion, disintegration of the vehicle, or associated formation of water channels. In some circumstances, the compound is dispersed in microcapsules (microspheres) or nanoparticles prepared from a suitable polymer, for example, 5-isobutyl 2-cyanoacrylate (see, for example, Michael et al., *J. Pharmacy Pharmacol.* 43, 1-5, (1991), and dispersed in a biocompatible dispersing medium, which yields sustained delivery and biological activity over a protracted time.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acidco-glycolic acid), poly(D-lactic acid-co-glycolic acid), and poly(L-lactic acid-coglycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (betahydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

Treatment

Disclosed herein are methods of treating a subject with a neurodegenerative disorder through administration of one or more of the disclosed compounds. The compounds can be administered by any appropriate route including orally, parenterally, or topically. In particular examples, sobetirome, or a pharmaceutically acceptable salt thereof, is administered orally. In certain examples, sobetirome, or a pharmaceutically acceptable salt thereof, is administered parenterally. In some embodiments, sobetirome, or a pharmaceutically acceptable salt thereof, is administered buccally, sublingually, sublabially, or by inhalation. In other embodiments, sobetirome, or a pharmaceutically acceptable salt thereof, is administered sublingually. In yet other embodiments, sobetirome, or a pharmaceutically acceptable salt thereof, is administered parenterally. In particular embodiments, sobetirome, or a pharmaceutically acceptable salt thereof, is administered intra-arterially, intravenously, intraventricularly, intramuscularly, subcutaneously, intraspinally, intraorbitally, intracranially or intrathecally.

The administration of a pharmaceutical composition comprising the disclosed compounds can be for prophylactic or therapeutic purposes. For prophylactic and therapeutic purposes, the treatments can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the treatments for viral infection can be provided as repeated doses within a prolonged prophylaxis or treatment regimen that will yield clinically significant results to alleviate one or more symptoms or detectable conditions associated with a neurodegenerative disorder.

An effective amount or concentration of the disclosed compounds may be any amount of a composition that alone, or together with one or more additional therapeutic agents, is sufficient to achieve a desired effect in a subject. The effective amount of the agent will be dependent on several factors, including, but not limited to, the subject being treated and the manner of administration of the therapeutic composition. In one example, a therapeutically effective amount or concentration is one that is sufficient to prevent advancement, delay progression, or to cause regression of a disease, or which is capable of reducing symptoms caused by any disease, including neurodegenerative disorders.

In one example, a desired effect is to reduce or inhibit one or more symptoms associated with a neurodegenerative disorder. The one or more symptoms do not have to be completely eliminated for the composition to be effective. For example, a composition can decrease the sign or symptom by a desired amount, for example by at least 20%, at least 50%, at least 80%, at least 90%, at least 95%, at least 98%, or even at least 100%, as compared to how the sign or symptom would have progressed in the absence of the composition or in comparison to currently available treatments.

The actual effective amount will vary according to factors such as the type of neurological disorder to be protected against/therapeutically treated and the particular status of the subject (for example, the subject's age, size, fitness, extent of symptoms, susceptibility factors, and the like) time and route of administration, other drugs or treatments being administered concurrently, as well as the specific pharmacology of treatments for viral infection for eliciting the desired activity or biological response in the subject. Dosage regimens can be adjusted to provide an optimum prophylactic or therapeutic response.

An effective amount is also one in which any toxic or detrimental side effects of the compound and/or other biologically active agent is outweighed in clinical terms by therapeutically beneficial effects. A non-limiting range for a therapeutically effective amount of treatments for viral infection within the methods and formulations of the disclosure is about 0.0001 μg/kg body weight to about 10 mg/kg body weight per dose, such as about 0.0001 μg/kg body weight to about 0.001 μg/kg body weight per dose, about 0.001 μg/kg body weight to about 0.01 μg/kg body weight per dose, about 0.01 μg/kg body weight to about 0.1 μg/kg body weight per dose, about 0.1 μg/kg body weight to about 10 μg/kg body weight per dose, about 1 μg/kg body weight to about 100 μg/kg body weight per dose, about 100 μg/kg body weight to about 500 μg/kg body weight per dose, about 500 μg/kg body weight per dose to about 1000 μg/kg body weight per dose, or about 1.0 mg/kg body weight to about 10 mg/kg body weight per dose.

Determination of effective amount is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art, including the EAE model of multiple sclerosis. Using such models, only ordinary calculations and adjustments are required to determine an appropriate concentration and dose to administer a therapeutically effective amount of the treatments for viral infection (for example, amounts that are effective to alleviate one or more symptoms of a neurodegenerative disorder).

EXAMPLES

The following examples are illustrative of the disclosed compounds. In light of this disclosure, those of skill in the art will recognize that variations of these examples and other examples of the disclosed compounds would be possible without undue experimentation.

Example 1—tert-butyl 2-(4-formyl-3,5-dimethylphenoxy)acetate (Compound 3)

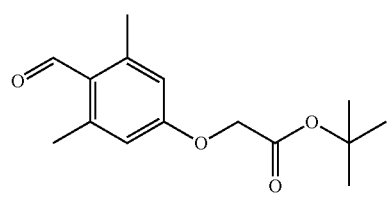 [SMILES: Cc1cc(OCC(=O)OC(C)(C)C)cc(C)c1C=O]

To a solution of 4-hydroxy-2,6-dimethylphenol (compound 2) (15.02 g, 100 mmol) and DMF (400 mL) was added Cs$_2$CO$_3$ (65.2 g, 200 mmol). The resulting mixture was cooled to 0° C. and t-butyl-chloroacetate (17.9 mL, 125 mmol) was slowly added. The reaction mixture was then stirred at room temperature for 3 hours and subsequently slowly poured into 800 mL H$_2$O. The resulting solution was stirred for 15 minutes at room temperature and then extracted with diethylether (3×500 mL). The combined organic fractions were washed with water (3×1 L), brine, dried with MgSO$_4$ and concentrated. Recrystallization of the residue with hexanes gave compound 3 (23.6 g, 89%). $^1$H NMR (400 MHz, CD$_3$OD): δ 10.43 (s, 1H), 6.65 (s, 2H), 4.65 (s, 2H), 2.58 (s, 6H), 1.49 (s, 9H). HRMS exact mass calcd for C$_{15}$H$_{21}$O$_4$ [M+H]$^+$: 265.14344. Found 265.14445.

Example 2—1-(benzyloxy)-4-iodo-2-isopropylbenzene (Compound 5)

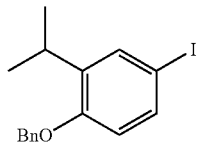 [SMILES: CC(C)c1cc(I)ccc1OCc1ccccc1]

To a stirring solution of 2-isopropylphenol (compound 4) (13.62 g, 100 mmol), sodium iodide (14.98 g, 100 mmol) and methanol (300 mL), was added 10 mL of a 10M NaOH solution. The reaction mixture was then cooled to 4° C. and a solution of NaOCl (6% aq, 129 mL, 115 mmol) was slowly added dropwise over 18 hours. The reaction mixture was then allowed to stir at room temperature for 2 hours. A 10% Na$_2$S$_2$O$_3$ solution (300 mL) was added followed by acidification of the solution to neutral pH with concentrated HCl. The solution was then extracted with diethyl ether (3×300 mL). The combined organic fractions were washed with brine, dried with MgSO$_4$ and concentrated. Purification of the residue with flash chromatography (silica, 0% to 75% dichloromethane/hexanes) gave 4-iodo-isopropylphenol (19.6 g, 75%). $^1$HNMR (400 MHz, CDCl$_3$) δ (ppm): 7.45 (1H, d, j=2 Hz), 7.35 (1H, dd, j=8.4 Hz, 2 Hz), 6.52 (1H, d, J=8.4 Hz), 3.14 (1H, septet, J=7.2 Hz), 1.23 (6H, d, J=7.2 Hz). To a solution of 4-iodo-isopropylphenol (16.18 g, 61.73 mmol) in DMF (200 mL) was added K$_2$CO$_3$ (25.6 g, 185.2 mmol) and benzyl bromide (92.6 mmol, 11 mL). The reaction mixture was then stirred at 75° C. for 16 hours. After cooling the solution the room temperature, the mixture was then slowly poured into 600 mL of H$_2$O and subsequently stirred at room temperature for 15 min. The mixture was then extracted with hexanes (3×500 mL). The combined organic fractions were washed with water (3×500 mL), brine, dried with Mg$_2$SO$_4$, and concentrated under reduced pressure. Purification of the residue with flash chromatography (silica, 0% to 2% ethyl acetate/hexanes) yielded compound 5 (16.7 g, 77%). $^1$HNMR (400 MHz, CDCl$_3$): δ 7.41-7.24 (m, 5H), 6.91 (d, 1H, J=2 Hz), 6.76 (d, 1H, J=8.4 Hz), 6.63 (m, 3H), 4.97 (s, 2H), 4.58 (s, 2H), 3.89 (s, 2H), 3.30 (sept, 1H, J=7.1 Hz), 2.17 (s, 6H), 1.14 (d, 6H, J=7.1 Hz).

Example 3—2-(4-(4-(benzyloxy)-3-isopropylbenzyl)-3,5-dimethylphenoxy)acetic Acid (Compound 6)

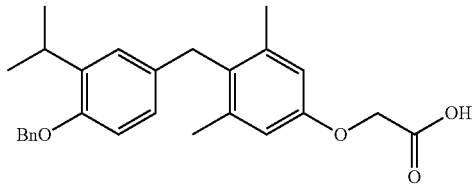 [SMILES: Cc1cc(OCC(=O)O)cc(C)c1Cc1ccc(OCc2ccccc2)c(C(C)C)c1]

A solution of 3 (16.2 g, 46 mmol), THF (180 mL), and 4 Å molecular sieves (3 g) was placed under reduced pressure for 1 minute and then placed under argon for 1 minute. This process was repeated three times to ensure a deoxygenated solution. The solution was then cooled to 0° C. and an iPrMgCl solution (2 M THF, 34.5 mL, 69 mmol) was added. The reaction mixture was then stirred at room temperature for 2.5 hours where it was then cooled to −78° C. A solution of 5 (9.36 g, 35.4 mmol) and THF (20 mL) was then added and the reaction mixture was stirred at −78° C. for 1 hour and at room temperature for 1 hour. The reaction was quenched with a 10% NH$_4$Cl (aq) solution (200 mL) and extracted with ethyl acetate (3×200 mL). The combined organic fractions were washed with brine, dried with Mg$_2$SO$_4$, and concentrated under reduced pressure. A HNMR was taken to confirm consumption of 5 and the resulting crude residue was then utilized in the subsequent reaction. The crude residue was dissolved in DCM (200 mL) and cooled to 0° C. Triethylsilane (28.3 mL, 177 mmol) was added followed by the slow addition of trifluoroacetic acid (40.7 mL, 531 mmol). The reaction mixture was then stirred at room temperature for 3 hours and then concentrated with reduced pressure. DCM (100 mL) was added and the solution was concentrated again with reduced pressure. This process was repeated two more times to remove the remaining TFA. Hexanes were added and the resulting mixture was cooled to 0° C. to precipitate the desired product (6) as a white solid (8.15 g, 55% (over two steps)). $^1$H NMR (400 MHz, CD$_3$OD): δ 7.41-7.24 (m, 5H), 6.91 (d, 1H, J=2 Hz), 6.76 (d, 1H, J=8.4 Hz), 6.63 (m, 3H), 4.97 (s, 2H), 4.58 (s, 2H), 3.89 (s, 2H), 3.30 (sept, 1H, J=7.1 Hz), 2.17 (s, 6H), 1.14 (d, 6H, J=7.1 Hz). HRMS exact mass calcd for C$_{27}$H$_{30}$O$_4$Na [M+Na$^+$]$^+$: m/z 441.20363. Found m/z 441.20463.

Example 4—Representative Procedure for Preparation of Acid Chloride (Compound 6a)

A solution of oxalyl chloride (200 μL, 2.33 mmol) in 2 mL of DCM was slowly added to a 0° C. solution of compound 6 (209 mg, 0.5 mmol) and DCM (4 mL). DMF (2 μL) was then added and the reaction mixture was stirred at room temperature for 3 hours. The solution was then concentrated under reduced pressure. DCM (4 mL) was added to the residue and the solution was concentrated again, this process was repeated once more. The crude residue was of sufficient purity and was used immediately in the subsequent ester couplings.

Example 5—Ethyl 2-(4-{[4-hydroxy-3-(propan-2-yl)phenyl)methyl]-3,5-dimethylphenoxy) acetate (Compound 7)

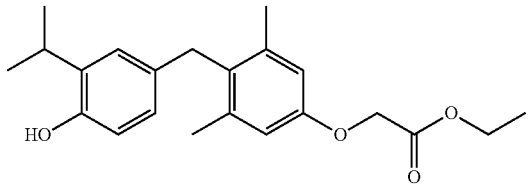 [SMILES: CCOC(=O)COc1cc(C)c(Cc2ccc(O)c(C(C)C)c2)c(C)c1]

To a stirred solution of compound 6 (209 mg, 0.5 mmol) in 2 mL ethanol was added 1 M HCl (ethanol) (15 mL, 15 mmol). The reaction mixture was stirred at room temperature for 24 hrs. The solution was then dried with $MgSO_4$ and concentrated under reduced pressure. The resulting residue was then dissolved in 5 mL of methanol and purged with argon. 10% Pd/C (50 mg) was added followed by the dropwise addition of triethylsilane (1.01 mL, 6.33 mmol). The reaction mixture was stirred at room temperature for 3 hrs and then filtered over a pad of celite with methanol. The solution was then concentrated under reduced pressure and purified with flash chromatography (silica, 0% to 2% ethyl acetate/hexanes) to yield 7 as an oil (113 mg, 62%). $^1H$ NMR (400 MHz, CDCl3): δ 6.91 (d, 1H, J=2 Hz), 6.62 (s, 2H), 6.60-6.54 (m, 2H), 4.60 (s, 2H), 4.59 (s, 1H), 4.29 (q, 2H, J=7.2 Hz), 3.89 (s, 2H), 3.15 (sept, 1H, J=7.1 Hz), 2.20 (s, 6H), 1.30 (t, 3H, J=7.2 Hz), 1.21 (d, 6H, J=7.1 Hz). HRMS exact mass calcd for $C_{22}H_{28}O_4Na$ [M+Na$^+$]$^+$: m/z 379.18798. Found m/z 379.18823.

Example 6—2-(trimethylamino)ethyl 2-(4-{[4-hydroxy-3-(propan-2-yl)phenyl]methyl}-3,5-dimethylphenoxy)acetate hydrobromide (Compound 8)

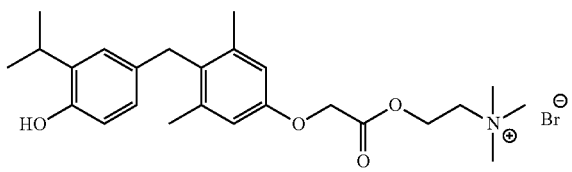 [SMILES: Cc1cc(OCC(=O)OCC[N+](C)(C)C)cc(C)c1Cc1ccc(O)c(C(C)C)c1 ; [Br-]]

To a solution of 6 (209 mg, 0.5 mmol) dissolved in DMF (5 mL) was added $K_2CO_3$ (138 mg, 1.0 mmol) followed by (2-Bromoethyl) trimethylammonium bromide (309 mg, 1.25 mmol). The reaction mixture was then stirred at rt for 72 hours and then filtered. The mixture was then directly purified with flash chromatography (silica, 0%, 5%, 10%, 20%, 30% methanol/dcm) to yield the desired product (121 mg). The residue was then dissolved in MeOH (4 mL) and purged with argon. 10% Pd/C (60 mg) was added followed by the dropwise addition of triethylsilane (479 μL, 3 mmol). The reaction mixture was stirred at room temperature for 4 hrs and then filtered over a pad of celite with methanol. The solution was then concentrated under reduced pressure and the resulting solid was isolated with ether to yield (8) (97 mg, 39% (two steps)). $^1H$ NMR (400 MHz, CD$_3$OD): δ 6.82 (d, 1H, J=2 Hz), 6.67 (s, 2H), 6.60 (d, 1H, J=8.2 Hz), 6.54 (dd, 1H, J=8.2 Hz, 2 Hz), 4.77 (s, 2H), 4.46 (m, 2H), 3.90 (s, 2H), 3.31 (m, 2H), 3.21 (sept, 1H, J=7 Hz), 2.22 (s, 6H), 1.14 (d, 6H, J=7 Hz). LRMS (ESI$^+$). Found 414.3 (M−Br)$^+$.

Example 7—2-(morpholin-4-yl)ethyl 2-(4-{[4-hydroxy-3-(propan-2-yl)phenyl]methyl}-3,5-dimethylphenoxy)acetate (Compound 9)

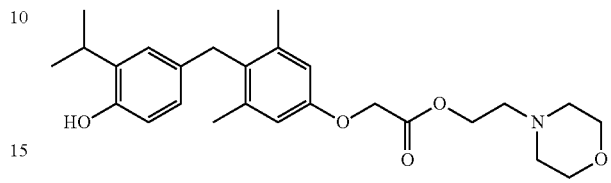

To a 0° C. solution of 4-(2-hydroxyethyl)morpholine (182 μL, 1.5 mmol), DMAP (122 mg, 1.0 mmol), and DCM (5 mL) was added a solution of 6a (0.5 mmol) and DCM (2 mL). The reaction mixture was allowed to warm to rt overnight. The reaction mixture was then concentrated, redissolved in a minimal amount of DCM, and purified using flash chromatography (silica, 0% to 4% MeOH/DCM). The resulting ester was then dissolved in 5 mL MeOH and purged with argon. 10% Pd/C (50 mg) was added followed by the dropwise addition of triethylsilane (799 μL, 5 mmol). The reaction mixture was stirred at room temperature for 4 hrs and then filtered over a pad of celite with methanol. The solution was then concentrated under reduced pressure and purified using flash chromatography (silica, 0% to 5% MeOH/DCM) to yield 9 as an oil (107 mg, 48% over two steps). $^1H$ NMR (400 MHz, CDCl$_3$): δ 6.92 (d, 1H, J=2 Hz), 6.55 (m, 4H), 4.55 (s, 2H), 4.36 (t, 2H, J=5.7 Hz), 3.87 (s, 2H), 3.70 (t, 4H, J=4.6 Hz), 3.19 (sept, 1H, J=7 Hz), 2.67 (t, 2H, J=5.7 Hz), 2.51 (t, 4H, J=4.6 Hz), 2.18 (s, 6H), 1.20 (d, 6H, J=7 Hz). HRMS exact mass calcd for $C_{26}H_{36}N_1O_5$ [M+H$^+$]$^+$: m/z 442.25880. Found m/z 442.25979.

Example 8—GC1-ethanolamine (Compound 11)

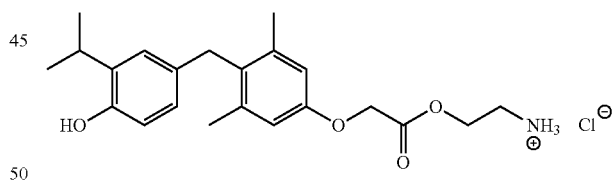

To a 0° C. solution of N-Boc-ethanolamine (161 mg, 1.0 mmol), DMAP (183 mg, 1.5 mmol), and DCM (5 mL) was added a solution of compound 6a (0.5 mmol) and DCM (2 mL). The reaction mixture was allowed to warm to rt overnight. The reaction mixture was then concentrated, redissolved in a minimal amount of DCM, and purified using flash chromatography (silica, 10% to 20% ethyl acetate/hexanes) to yield compound 10 (72%, 0.36 mmol). The resulting ester (compound 10) (200 mg, 0.36 mmol) was dissolved in 4 mL MeOH and purged with argon. 10% Pd/C (40 mg) was added followed by the dropwise addition of triethylsilane (569 μL, 3.56 mmol). The reaction mixture was stirred at room temperature for 4 hrs and then filtered over a pad of celite with methanol. The solution was then concentrated under reduced pressure and purified using flash chromatography (silica, 10% to 30% ethyl acetate/hexanes)

to the debenzylated product as an oil (112 mg). The resulting oil (112 mg, 0.237 mmol) was dissolved in ethyl acetate (2 mL) and 3 mL of 1 N HCl (ethyl acetate) was added. The reaction mixture was then stirred at room temperature overnight, concentrated under reduced pressure, and resulting solid 11 was collected with diethyl ether (75 mg, 51% (over two steps)). $^1$H NMR (400 MHz, CD$_3$OD): δ 6.82 (d, 1H, J=2 Hz), 6.67 (s, 2H), 6.60 (d, 1H, J=8.2 Hz), 6.54 (dd, 1H, J=8.2 Hz, 2 Hz), 4.77 (s, 2H), 4.46 (m, 2H), 3.90 (s, 2H), 3.31 (m, 2H), 3.21 (sept, 1H, J=7 Hz), 2.22 (s, 6H), 1.14 (d, 6H, J=7 Hz). HRMS exact mass calcd for C$_{22}$H$_{30}$N$_1$O$_4$[M−Cl$^-$]$^+$: m/z 372.21693. Found m/z 372.21807.

Example 9—Benzyl Protected Ethanolamine: (Compound 12)

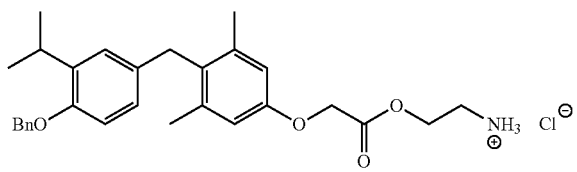 [SMILES: Cc1cc(OCC(=O)OCC[NH3+])cc(C)c1Cc1ccc(OCc2ccccc2)c(C(C)C)c1 ; [Cl-]]

To a solution of compound 10 (200 mg, 0.356 mmol) in ethyl acetate (2 mL) was added 10 mL of 1 N HCl (ethyl acetate). The reaction mixture was then stirred at room temperature overnight, concentrated under reduced pressure, and resulting white solid (compound 12) was collected with diethyl ether (143 mg, 81%). $^1$H NMR (400 MHz, CD$_3$OD): δ 7.45-7.29 (m, 5H), 6.92 (d, 1H, J=2 Hz), 6.83 (d, 1H, J=8.4 Hz), 6.71-6.65 (m, 3H), 5.03 (s, 2H), 4.78 (s, 2H), 4.47 (t, 2H, J=5 Hz), 3.94 (s, 2H), 3.33 (m, 3H), 2.21 (s, 6H), 1.16 (d, 6H, J=7.1 Hz). HRMS exact mass calcd for C$_{22}$H$_{30}$N$_1$O$_4$ [M−Cl$^-$]$^+$: m/z 462.26389. Found m/z 462.26450.

Example 10—2-(2,6-diaminohexanamido)ethyl 2-(4-{[4-(benzyloxy)-3-(propan-2-yl)phenyl]methyl}-3,5-dimethylphenoxy)acetate (Compound 13)

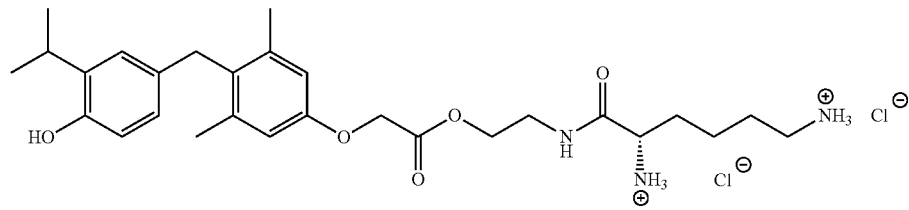 [SMILES: Cc1cc(OCC(=O)OCCNC(=O)[C@@H]([NH3+])CCCC[NH3+])cc(C)c1Cc1ccc(O)c(C(C)C)c1 ; [Cl-] ; [Cl-]]

To a solution of Boc-Lys(Boc)-OH (106 mg, 0.2 mmol) and DMF (2 mL) was added EDCl—HCl (38 mg, 0.2 mmol) and HoBt-H$_2$O (31 mg, 0.2 mmol). The reaction mixture was stirred at room temperature for 30 min. DIEA (87 μL, 0.5 mmol) was added to the reaction mixture followed by compound 11 (50 mg, 0.1 mmol) and the reaction mixture was stirred at room temperature overnight. The mixture was then poured into H$_2$O (20 mL) and extracted with ethyl acetate (3×20 mL). The combined organic layers were then washed with sat. NaHCO$_3$, 1M HCl, and brine. After drying the organic layer with MgSO$_4$, the ethyl acetate was concentrated using reduced pressure and purified via flash chromotagraphy (silica, 0% to 2.5% DCM/MeOH). The residue was dissolved in 4 mL MeOH and purged with argon. 10% Pd/C (100 mg) was added followed by the dropwise addition of triethylsilane (320 μL, 2 mmol). The reaction mixture was stirred at room temperature for 4 hrs and then filtered over a pad of celite with methanol. The methanol solution was then concentrated and hexanes was added to the round bottomed flask. A white solid appeared on the walls of the round bottomed flask, and the resulting hexanes layer was decanted. This process was repeated two more times. The resulting solid was dissolved in 1 mL of ethyl acetate and to this solution was added 4 mL of 1M HCl (ethyl acetate). The reaction mixture was stirred at rt overnight and then concentrated using reduced pressure. Diethyl ether was added and the resulting solid was collected to give compound 13 (23 mg, 40%). $^1$H NMR (400 MHz, CD$_3$OD): δ 6.81 (d, 1H, J=2 Hz), 6.67 (s, 2H), 6.60 (d, 1H, J=8.2 Hz), 6.52 (dd, 1H, J=8.2 Hz, 2 Hz), 4.73 (s, 2H), 4.41 (m, 1H), 4.30 (m, 1H), 3.89 (m, 3H), 3.62 (m, 3H), 3.20 (sept, 1H, J=6.70 Hz), 2.96 (t, 2H, J=7.2 Hz), 2.21 (s, 6H), 1.90 (m, 2H), 1.73 (m, 2H), 1.51 (m, 2H), 1.13 (d, 6H, J=6.70 Hz). HRMS exact mass calcd for C$_{28}$H$_{42}$N$_3$O$_5$ [M−2Cl$^-$−H$^+$]$^+$: m/z 500.31190. Found m/z 500.31243.

Example 11—2-(2-amino-4-methylpentanamido) ethyl 2-(2-{[4-(benzyloxy)-3-(propan-2-yl)phenyl]methyl}-3,5-dimethylphenoxy)acetate (Compound 14)

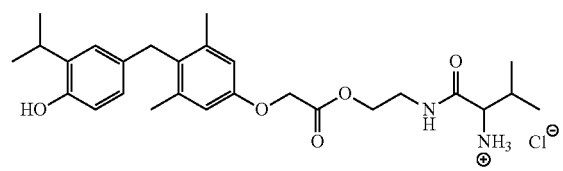 [SMILES: Cc1cc(OCC(=O)OCCNC(=O)C([NH3+])C(C)C)cc(C)c1Cc1ccc(O)c(C(C)C)c1 ; [Cl-]]

To a solution of (Boc)-Valine-OH (60 mg, 0.274 mmol) and DMF (5 mL) was added EDCl—HCl (53 mg, 0.274 mmol) and HoBt—H$_2$O (42 mg, 0.274 mmol). The reaction mixture was stirred at room temperature for 30 min. DIEA (119 μL, 0.685 mmol) was added to the reaction mixture followed by compound 11 (68 mg, 0.137 mmol) and the reaction mixture was stirred at rt overnight. The mixture was then poured into H$_2$O (30 mL) and extracted with ethyl acetate (3×30 mL). The combined organic layers were then washed with sat. NaHCO$_3$, 1M HCl, and brine. After drying the organic layer with MgSO$_4$, the ethyl acetate was concentrated using reduced pressure and purified via flash chromotagraphy (silica, 50% ethyl acetate/hexanes). The residue was dissolved in 3 mL MeOH and purged with argon. 10% Pd/C (30 mg) was added followed by the dropwise addition of triethylsilane (320 μL, 2 mmol). The reaction mixture was stirred at room temperature for 4 hrs and then filtered over a pad of celite with methanol. The methanol solution was then concentrated and purified with flash chromatography (silica, 30% to 50% ethyl acetate/hexanes). The resulting residue was dissolved in 1 mL of ethyl acetate and to this solution was added 4 mL of 1M HCl (ethyl acetate). The reaction mixture was stirred at rt overnight and then concentrated using reduced pressure. Diethyl ether was added and the resulting solid was collected to give compound 14 (24 mg, 32% overall yield). $^1$H NMR (400 MHz, CD$_3$OD): δ 8.58 (m, 1H), 7.92 (s, 1H), 6.82 (d, 1H, J=2 Hz), 6.66 (s, 2H), 6.60 (d, 1H, J=8.2 Hz), 6.54 (dd, 1H, J=8.2 Hz, 2 Hz), 4.70 (s, 2H), 4.33 (m, 2H), 3.90 (s, 2H), 3.66 (m, 2H), 3.50 (m, 2H), 3.20 (sept, 1H, J=6.70 Hz), 2.21 (s, 6H), 1.14 (d, 6H, J=6.70 Hz), 1.07 (m, 6H). HRMS exact mass calcd for C$_{27}$H$_{39}$N$_2$O$_5$[M+H$^+$]$^+$: m/z 471.28535. Found m/z 471.28686.

Example 12—azetidin-3-yl 2-(4-{[4-hydroxy-3-(propan-2-yl)phenyl]methyl}-3,5-dimethylphenoxy-lacetate (Compound 15)

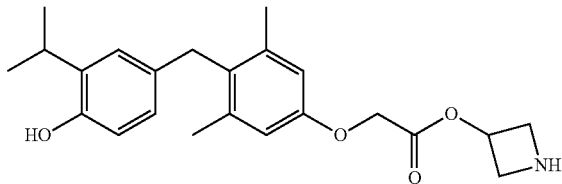 [SMILES: Cc1cc(OCC(=O)OC2CNC2)cc(C)c1Cc1ccc(O)c(C(C)C)c1]

To a 0° C. solution of 1-(tert-butylcarbonyl)-3-hydroxyazetidine (260 mg, 1.5 mmol), DMAP (183 mg, 1.5 mmol), and DCM (5 mL) was added a solution of the acid chloride generated from compound 6 (0.5 mmol) and DCM (2 mL). The reaction mixture was allowed to warm to rt overnight. The reaction mixture was then concentrated, redissolved in a minimal amount of DCM, and purified using flash chromotagraphy (silica, 10% to 30% ethyl acetate/hexanes). The resulting ester (242 mg, 0.422 mmol) was dissolved in 5 mL MeOH and purged with argon. 10% Pd/C (90 mg) was added followed by the dropwise addition of triethylsilane (1.01 mL, 6.33 mmol). The reaction mixture was stirred at room temperature for 4 hrs and then filtered over a pad of celite with methanol. The solution was then concentrated under reduced pressure and purified using flash chromatography (silica, 10% to 30% ethyl acetate/hexanes) to yield the desired product as an oil (106 mg, 51% over two steps). The resulting residue was dissolved in ethyl acetate (3 mL) and 5 mL of 1 N HCl (ethyl acetate) was added. The reaction mixture was then stirred at room temperature overnight, concentrated under reduced pressure, and resulting solid was collected with hexanes. The solid was then purified using flash chromotagraphy (silica, 0% to 10% methanol/(dcm+1% isopropylamine)) to yield compound 15 (101 mg, 45% overall yield). $^1$HNMR (400 MHz, CD$_3$OD): δ 6.80 (d, 1H, J=2 Hz), 6.65 (s, 2H), 6.60 (d, 1H, J=8.2 Hz), 6.52 (dd, 1H, J=8.2 Hz, 2 Hz), 5.44 (m, 1H), 4.78 (s, 2H), 4.45 (m, 2H), 4.18 (m, 2H), 3.88 (s, 2H), 3.20 (sept, 1H, J=6.95 Hz), 2.20 (s, 6H), 1.13 (d, 6H, J=6.95 Hz). HRMS exact mass calcd for C$_{23}$H$_{30}$N$_1$O$_4$ [M+H$^+$]$^+$: m/z 384.21693. Found m/z 384.21735.

Example 13—2-amino-3-(4-{[2-(4-{[4-hydroxy-3-(propan-2-yl)phenyl]methyl}-3,5-dimethylphenoxy) acetyl]oxy}phenyl)propanoic Acid (Compound 16)

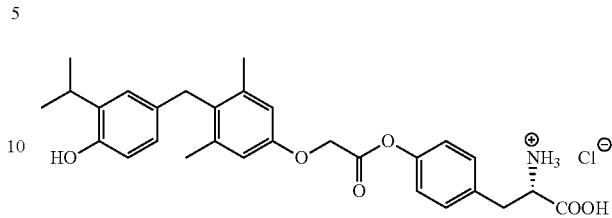

To a solution of N-t-boc-L-tyrosine (281 mg, 1 mmol) and acetone (4 mL) was added 1 N NaOH (aq) (2 mL, 2 mmol). This reaction mixture was then cooled to 0° C. and a solution of the acid chloride generated from (compound 6) (0.5 mmol) and acetone (2 mL) was added dropwise. The reaction mixture was allowed to warm to r.t. overnight. To the reaction mixture was added 30 mL of 1 N HCl and the mixture was extracted with ethyl acetate (3×30 mL). The combined organic layers were then washed with brine, dried, and concentrated under reduced pressure. The crude residue was then purified with flash chromatography (silica, 0% to 5% methanl/dcm+1% acetic acid). The residue was dissolved in 4 mL MeOH and purged with argon. 10% Pd/C (40 mg) was added followed by the dropwise addition of triethylsilane (479 µL, 3 mmol). The reaction mixture was stirred at room temperature for 4 hrs and then filtered over a pad of celite with methanol. The methanol solution was then concentrated and purified with flash chromatagraphy (silica, 0% to 5% methanl/dcm+1% acetic acid). The resulting residue was dissolved in 2 mL of ethyl acetate and to this solution was added 3 mL of 1M HCl (ethyl acetate). The reaction mixture was stirred at rt overnight and then concentrated using reduced pressure. Diethyl ether was added and the resulting solid was collected to give compound 16 (33 mg, 12.5% (overall for three steps)). $^1$H NMR (400 MHz, DMSO-D$_6$): δ 7.32 (d, 2H, J=8.5 Hz), 7.14 (d, 2H, J=8.5 Hz), 6.83 (d, 1H, j=2 Hz), 6.71 (s, 2H), 6.61 (d, 1H, J=8.2 Hz), 6.46 (dd, 1H, J=8.2, 2 Hz), 5.01 (s, 2H), 4.17 (t, 1H, J=6.5 Hz), 3.8 (s, 2H), 3.11 (m, 3H), 2.18 (s, 6H), 1.08 (d, 6H, J=6.8 Hz). HRMS exact mass calcd for C$_{29}$H$_{34}$N$_1$O$_6$ [M−Cl$^-$]$^+$: m/z 492.23806. Found m/z 492.23738.

Example 14—[(2R,3S,4S,5R,6R)-3,4,5,6-tetrahydroxyoxan-2-yl]methyl 2-(4-{[4-hydroxy-3-(propan-2-yl)phenyl]methyl}-3,5-dimethylphenoxy)acetate (Compound 18)

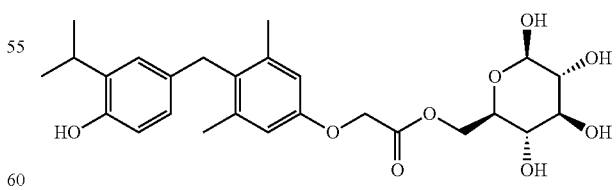

To a 0° C. solution of 17 (306 mg, 0.566 mmol), DMAP (175 mg, 1.43 mmol), and DCM (4 mL) was added a solution of the acid chloride generated from 6 (0.714 mmol) and DCM (3 mL).

The reaction mixture was allowed to warm to rt overnight. The reaction mixture was then concentrated under reduced pressure and purified with flash chromotography (silica, 10% to 30% ethyl acetate/hexanes) to yield 377 mg of purified product. This product (279 mg, 0.296 mmol) was then dissolved in acetic acid (10 mL) and THF (5 mL) and purged with argon. 10% Pd/C (300 mg) was added followed by the dropwise addition of triethylsilane (2.84 mL, 17.8 mmol). The reaction mixture was stirred at room temperature for 40 hrs and then filtered over a pad of celite with methanol. The methanol solution was then concentrated under reduced pressure. To this solution (acetic acid remained) was added hexanes and concentrated again under reduced pressure, this was repeated five more times. Lastly, the white solid was collected with hexanes to yield 18 (123 mg, 85% (44% overall yield)). $^1$HNMR (400 MHz, CD$_3$OD) δ: 6.82 (d, 1H, j=2 Hz), 6.64 (s, 2H), 6.58 (d, 1H, J=8.15 Hz), 6.52 (dd, 1H, J=8.15, 2 Hz), 5.10 (d, 1H, J=3.75 Hz), 4.68 (m, 2H), 4.50 (m, 2H), 4.33 (m, 1H), 4.00 (m, 1H), 3.88 (s, 2H), 3.65 (m, 1H), 3.20 (m, 2H), 2.19 (s, 6H), 1.29 (d, 2H, J=6.59 Hz), 1.08 (d, 6H, J=6.94 Hz). HRMS exact mass calcd for C$_{26}$H$_{35}$N$_1$O$_9$ [M+H$^+$]$^+$: m/z 491.22756. Found m/z 491.22775.

Example 15—2-(dimethylamino)ethyl 2-(4-{[4-hydroxy-3-(propan-2-yl)phenyl]methyl}-3,5-dimethylphenoxy)acetate (Compound 19)

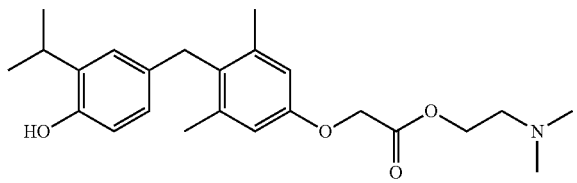 [SMILES: Cc1cc(OCC(=O)OCCN(C)C)cc(C)c1Cc1ccc(O)c(C(C)C)c1]

To a 0° C. solution of Dimethylethanolamine (150 uL, 1.5 mmol), DMAP (92 mg, 0.5 mmol), NEt$_3$ (208 uL, 1.5 mmol) and DCM (4 mL) was added a solution of the acid chloride generated from 6 (0.5 mmol) and DCM (5 mL). The reaction mixture was allowed to warm to rt overnight. The reaction mixture was then concentrated under reduced pressure and purified with flash chromotography (silica, 0% to 5% MeOH/DCM) to yield 40 mg of purified product. This product (279 mg, 0.296 mmol) was then dissolved in acetic acid (750 uL) and THF (375 mL) and purged with argon. 10% Pd/C (40 mg) was added followed by the dropwise addition of triethylsilane (253 mL, 1.59 mmol). The reaction mixture was stirred at room temperature for 4 hrs and then filtered over a pad of celite. The solution was then concentrated under reduced pressure. To this solution (acetic acid remained) was added hexanes and concentrated again under reduced pressure, this was repeated five more times. Lastly, the white solid was collected with hexanes to yield 19 (21 mg, (11% overall yield)). $^1$HNMR (400 MHz, CDCl$_3$) δ: 6.94 (d, 1H, J=2 Hz), 6.61 (s, 2H), 6.58 (m, 2H), 4.62 (s, 2H), 4.35 (t, 2H, J=5.56 Hz), 3.90 (s, 2H), 3.20 (sept, 1H, J=6.82 Hz), 2.66 (t, 2H, J=5.56 Hz), 2.32 (s, 6H), 2.21 (s, 6H), 1.23 (d, 2H, J=6.84 Hz). HRMS exact mass calcd for C$_{24}$H$_{31}$N$_1$O$_4$ [M+H$^+$]$^+$: m/z 400.24824. Found m/z 400.24905.

Example 16—1-methylazetidin-3-yl 2-(4-{[4-hydroxy-3-(propan-2-yl)phenyl]methyl}-3,5-dimethylphenoxy)acetate (Compound 20)

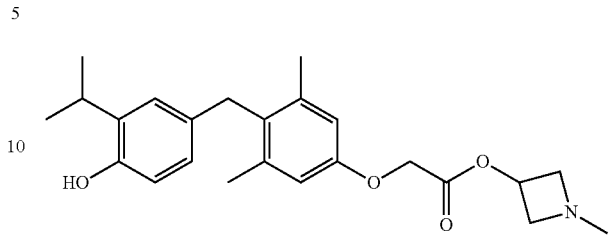

To a 0° C. solution of 1-(tert-butylcarbonyl)-3-hydroxyazetidine (260 mg, 1.5 mmol), DMAP (183 mg, 1.5 mmol), and DCM (5 mL) was added a solution of the acid chloride generated from 6 (0.5 mmol) and DCM (2 mL). The reaction mixture was allowed to warm to rt overnight. The reaction mixture was then concentrated, redissolved in a minimal amount of DCM, and purified using flash chromotagraphy (silica, 10% to 30% ethyl acetate/hexanes). The resulting ester was dissolved in DCM (5 mL) and Et$_3$SiH (80 uL) was added. The solution was then cooled to 0° C. and treated with TFA (574 uL, 7.5 mmol) and stirred at room temperature for 2 hours. The solution was then concentrated under reduced pressure and the product was precipitated from the solution with diethyl ether to yield the product as a white solid (177 mg, 60%). The isolated benzyl-protected intermediate (20a) (40 mg, 0.0681 mmol) was dissolved in AcOH (1 mL) and paraformaldehyde (41 mg, 1.36 mmol) was added followed by 10% Pd/C (40 mg). To this solution was added Et$_3$SiH (325 uL, 2.04 mmol) dropwise and the reaction mixture was stirred at room temperature for 4 hours and filtered over a pad of celite. Ethyl acetate was added to the solution and the resulting organic layer was washed 2× with sat. NaHCO$_3$, and 1× with water, followed by Brine. The organic layer was then dried with MgSO$_4$ and concentrated under reduced pressure. The product was isolated as a white solid with hexanes (12 mg, 44%). $^1$HNMR (400 MHz, CDCl$_3$): δ 6.94 (d, 1H, J=2 Hz), 6.62 (s, 2H), 6.56 (m, 2H) 5.18 (p, 1H, J=5.56 Hz), 4.63 (s, 2H), 3.90 (s, 2H), 3.76 (m, 2H), 3.20 (m, 3H), 2.41 (s, 3H), 2.22 (s, 6H), 1.23 (d, 6H, J=7.07 Hz). HRMS exact mass calcd for C$_{24}$H$_{32}$N$_1$O$_4$ [M+H$^+$]$^+$: m/z 398.23258. Found m/z 398.23307.

Example 17—pyrrolidin-2-ylmethyl 2-(4-{[4-hydroxy-3-(propan-2-yl)phenyl]methyl}-3,5-dimethylphenoxy)acetate (Compound 21)

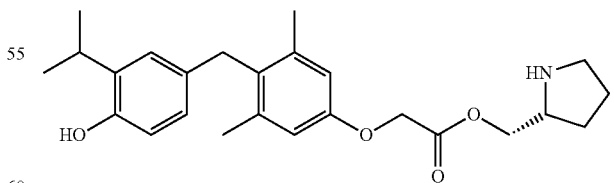

To a 0° C. solution of N-Boc-L-prolinol (252 mg, 1.25 mmol), DMAP (183 mg, 1.5 mmol), and DCM (3 mL) was added a solution of 6a (0.25 mmol) and DCM (2 mL). The reaction mixture was allowed to warm to rt overnight. The reaction mixture was then concentrated, redissolved in a minimal amount of DCM, and purified using flash chromotagraphy (silica, 10% to 20% ethyl acetate/hexanes) to yield the coupled N-boc ester. The resulting ester was dissolved in 4 mL MeOH and purged with argon. 10% Pd/C (50 mg) was added followed by the dropwise addition of triethylsilane (599 uL, 3.75 mmol). The reaction mixture was stirred at room temperature for 4 hrs and then filtered over a pad of celite with methanol. The solution was then concentrated under reduced pressure and purified using flash chromotagraphy (silica, 10% to 30% ethyl acetate/hexanes) to yield the debenzylated product as an oil. The resulting oil was dissolved in ethyl acetate (2 mL) and Et$_3$SiH (0.25 mmol, 40 uL) was added followed by 1 N HCl (ethyl acetate) (4 mL). The reaction mixture was then stirred at room temperature overnight, concentrated under reduced pressure, and resulting solid 11 was collected with diethyl ether (52 mg, 47% (over three steps)). $^1$HNMR (400 MHz, CDCl$_3$): δ 6.94 (d, 1H, J=2 Hz), 6.62 (s, 2H), 6.61 (d, 1H, J=8.08 Hz), 6.55 (dd, 1H, J=8.08 Hz, 2.02 Hz), 4.66 (m, 2H), 4.27 (m, 1H), 3.91 (s, 2H), 3.76-3.50 (m, 4H), 3.19 (sept, 1H, J=6.82 Hz), 2.23 (s, 6H), 2.11-1.86 (m, 3H), 1.65 (m, 1H), 1.23 (d, 6H, J=6.82 Hz). HRMS exact mass calcd for C$_{25}$H$_{34}$N$_1$O$_4$ [M+H$^+$]$^+$: m/z 412.24824. Found 412.24878 m/z.

Example 18—3-methyazetidin-3-yl 2-(4-{[4-hydroxy-3-(propan-2-yl)phenyl]methyl}-3,5-dimethylphenoxy)acetate (Compound 22)

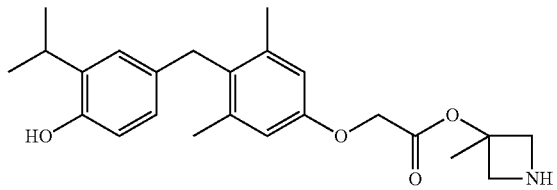 [SMILES: Cc1cc(OCC(=O)OC2(C)CNC2)cc(C)c1Cc1ccc(O)c(C(C)C)c1]

Followed procedure for the synthesis of (21) except with 1-Boc-3-Hydroxy-3-methylazetidine, THF, and heating during the coupling step (45° C.) yielded a white solid (22 mg, 22% overall yield). $^1$HNMR (400 MHz, CDCl$_3$): δ 6.94 (d, 1H, J=2 Hz), 6.62 (m, 3H), 6.51 (dd, 1H, J=8.08 Hz, 2.02 Hz), 4.64 (m, 2H), 4.35 (br, 2H), 4.10 (br, 2H), 3.90 (s, 2H), 3.18 (sept, 1H, J=7.07 Hz), 2.22 (s, 6H), 1.81 (s, 3H), 1.22 (d, 6H, J=6.82 Hz). HRMS exact mass calcd for C$_{24}$H$_{32}$N$_1$O$_4$ [M+H$^+$]$^+$: m/z 398.23258. Found m/z 398.23363.

Example 19—piperidin-4-yl 2-(4-{[4-hydroxy-3-(propan-2-yl)phenyl]methyl}-3,5-dimethylphenoxy)acetate (Compound 23)

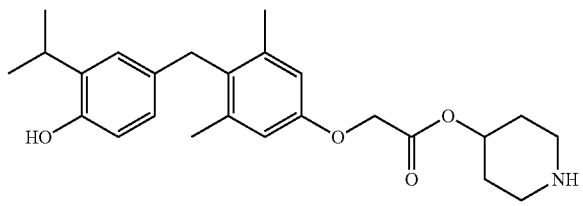 [SMILES: Cc1cc(OCC(=O)OC2CCNCC2)cc(C)c1Cc1ccc(O)c(C(C)C)c1]

Followed procedure for the synthesis of (21) except with 1-Boc-4-hydroxypiperidine and yielded a white solid (52 mg, 50% overall yield). $^1$HNMR (400 MHz, CDCl$_3$): δ 6.94 (d, 1H, J=2 Hz), 6.62 (s, 2H), 6.55 (d, 1H, J=8.08 Hz), 6.52 (dd, 1H, J=8.08 Hz, 2.02 Hz), 5.03 (sept, 1H, J=4.4 Hz), 4.62 (s, 2H), 3.90 (s, 2H), 3.21 (sept, 1H, J=6.82 Hz), 3.05 (m, 2H), 2.74 (m, 2H), 2.22 (s, 6H), 1.94 (m, 2H), 1.62 (m, 2H), 1.23 (d, 6H, J=6.82 Hz). HRMS exact mass calcd for C$_{25}$H$_{34}$N$_1$O$_4$ [M+H$^+$]$^+$: m/z 412.24824. Found m/z 412.24886.

Example 20—piperidin-3-yl 2-(4-{[4-hydroxy-3-(propan-2-yl)phenyl]methyl}-3,5-dimethylphenoxy)acetate (Compound 24)

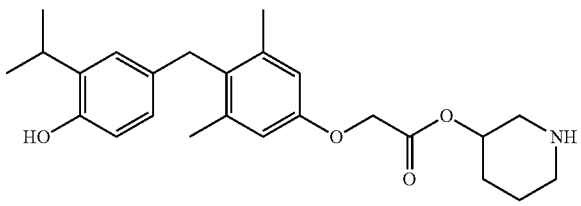 [SMILES: Cc1cc(OCC(=O)OC2CCCNC2)cc(C)c1Cc1ccc(O)c(C(C)C)c1]

Followed procedure for the synthesis of (21) except with 1-Boc-3-hydroxypiperidine and yielded a white solid (37 mg, 36% overall yield). $^1$HNMR (400 MHz, CDCl$_3$): δ 6.94 (d, 1H, J=2 Hz), 6.61 (s, 2H), 6.52 (d, 1H, J=8.08 Hz), 6.49 (dd, 1H, J=8.08 Hz, 2.02 Hz), 4.95 (m, 1H), 4.60 (d, 2H, J=1.52 Hz), 3.87 (s, 2H), 3.22 (sept, 1H, J=7.07 Hz), 3.02 (dd, 1H, J=13 Hz, 2.78 Hz)), 2.87 (dd, 1H, J=13.14 Hz, 5.81 Hz), 2.80 (t, 2H, J=5.05 Hz), 2.20 (s, 6H), 1.88 (m, 1H), 1.81-1.68 (m, 2H), 1.51 (m, 1H), 1.21 (d, 6H, J=6.82 Hz). HRMS exact mass calcd for C$_{25}$H$_{34}$N$_1$O$_4$ [M+H$^+$]$^+$: m/z 412.24824. Found m/z 412.24845.

Example 21—1-amino-2-methlpropan-2-yl 2-(4-{[4-hydroxy-3-(propan-2-yl)phenyl]methyl}-3,5-dimethylphenoxy)acetate (Compound 25)

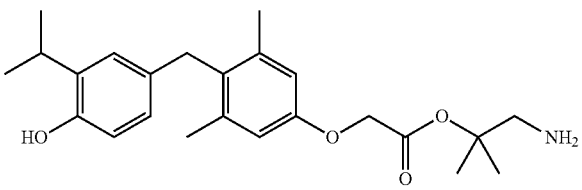 [SMILES: Cc1cc(OCC(=O)OC(C)(C)CN)cc(C)c1Cc1ccc(O)c(C(C)C)c1]

To a 0° C. solution of N-Cbz-1-amino-2-methylpropan-2-ol (223 mg, 1 mmol), DMAP (92 mg, 0.75 mmol), and THF (3 mL) was added a solution of 6a (0.25 mmol) and THF (2 mL). The reaction mixture was allowed stir at 45° C. overnight. The reaction mixture was then concentrated, redissolved in a minimal amount of DCM, and purified using flash chromotagraphy (silica, 20% to 50% ethyl acetate/hexanes) to yield the coupled N-Cbz ester (37 mg, 0.059 mmol). The resulting ester was dissolved in 2 mL MeOH and 2 mL of THF and purged with argon. 10% Pd/C (50 mg) was added followed by the dropwise addition of triethylsilane (283 uL, 1.77 mmol). The reaction mixture was stirred at room temperature for 3 hrs and then filtered over a pad of celite with methanol. The solution was then concentrated under reduced pressure and precipitated with hexanes and ether to yield the product as an oily residue (5.6 mg, 5.6% overall). $^1$HNMR (400 MHz, CDCl$_3$): δ 7.04 (m, 1H), 6.94 (d, 1H, J=2 Hz), 6.66 (s, 2H), 6.62 (d, 1H, J=8.08 Hz), 6.54 (dd, 1H, J=8.08 Hz, 2.02 Hz), 5.06 (br, 1H), 4.55 (s, 2H), 3.92 (s, 2H), 3.38 (d, 2H, J=6.32 Hz), 3.19 (sept, 1H, J=6.82 Hz), 2.23 (s, 6H), 2.20 (br, 1H), 1.25 (s, 6H), 1.23 (d, 6H, J=6.82 Hz). HRMS exact mass calcd for $C_{24}H_{34}N_1O_4$ $[M+H^+]^+$: m/z 400.24824. Found m/z 400.24765.

Example 22—3-(trifluoromethyl)azetidin-3-yl 2-(4-{[4-hydroxy-3-(propan-2-yl)phenyl]methyl}-3,5-dimethylphenoxy)acetate (Compound 26)

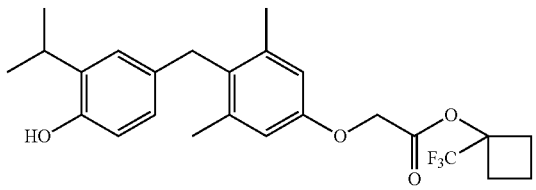 [SMILES: Cc1cc(OCC(=O)OC2(C(F)(F)F)CCC2)cc(C)c1Cc1ccc(O)c(C(C)C)c1]

To a 0° C. solution of N-Cbz-1-amino-3-hydroxy-3-(trifluoromethyl)-azetidine HCl (250 mg, 1.41 mmol), DMAP (122 mg, 1 mmol), and THF (3 mL) was added a solution of 6a (0.25 mmol) and THF (2 mL). The reaction mixture was allowed stir at 45° C. overnight. The reaction mixture was then concentrated, redissolved in a minimal amount of DCM, and purified using flash chromotagraphy (silica, 20% to 50% ethyl acetate/hexanes) to yield the coupled N-Cbz ester (75 mg, 0.121 mmol). The resulting ester was dissolved in 2 mL MeOH and 2 mL of THF and purged with argon. 10% Pd/C (50 mg) was added followed by the dropwise addition of triethylsilane (484 uL, 3.03 mmol). The reaction mixture was stirred at room temperature for 3 hrs and then filtered over a pad of celite with methanol. The solution was then concentrated under reduced pressure and precipitated with hexanes and ether to yield the product as an oily residue (6.8 mg, 6.0% overall). $^1$HNMR (400 MHz, CD$_3$OD): δ 6.82 (d, 1H, J=2 Hz), 6.67 (s, 2H), 6.59 (d, 1H, J=8.08 Hz), 6.52 (dd, 1H, J=8.08 Hz, 2.02 Hz), 4.78 (br s, 4H), 3.90 (s, 2H), 3.62 (t, 2H, J=5.86 Hz), 3.21 (sept, 1H, J=7.02 Hz), 2.21 (s, 6H), 1.23 (d, 6H, J=7.02 Hz).

Example 23—2-((2-(4-(4-hydroxy-3-isopropylbenzyl)-3,5-dimethylphenoxy)acetoxy)methyl)piperidin-1-ium Chloride (Compound 27)

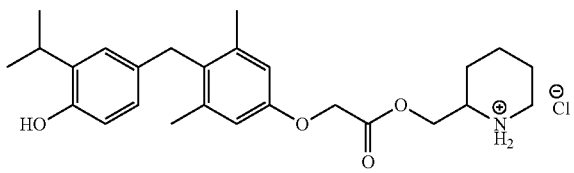 [SMILES: Cc1cc(OCC(=O)OCC2CCCC[NH2+]2)cc(C)c1Cc1ccc(O)c(C(C)C)c1 ; [Cl-]]

To a 0° C. solution of 1-(tert-butylcarbonyl)-2-(hydroxymethyl)piperidine (296 mg, 1.25 mmol), DMAP (183 mg, 1.5 mmol), and DCM (6 mL) was slowly added a solution of the acid chloride generated from 6 (0.5 mmol) in 4 mL DCM. The reaction mixture was allowed to warm to room temperature overnight with stirring. Evaporation of the resulting mixture gave a light-yellow oil which was purified using flash chromatography (silica, 10% to 30% ethyl acetate/hexanes). The resulting ester (288 mg, 0.468 mmol, 94% yield) was dissolved in 5 mL of dry methanol with 1 mL THF and 10% Pd/C (100 mg) was added to generate a suspension. The reaction mixture was subjected to vacuum for approximately 1 min, then placed under argon for approximately 1 min. This process was repeated three times to ensure the mixture was properly degassed. Triethylsilane (1.2 mL, 7.53 mmol) was then added dropwise to the suspension and the reaction mixture was stirred for 4 hrs at room temperature. Filtration over a pad of celite with methanol, concentration in vacuo, and purification via flash chromatography (silica, 10% to 30% ethyl acetate/hexanes) gave the desired product as an oil (129 mg, 0.245 mmol, 52% yield). The product oil (129 mg, 0.245 mmol) was dissolved in 5 mL ethyl acetate and 3 mL of 1 N HCl in ethyl acetate was added, followed by the addition of triethylsilane (39 μL, 0.245 mmol). The reaction mixture was stirred overnight at room temperature, concentrated under vacuum, and precipitated with hexanes to give the product 27 as a white solid (92 mg, 0.199 mmol, 81% yield, 40% overall yield). $^1$H NMR (400 MHz, CD$_3$OD): δ 6.76 (s, 1H), 6.61 (s, 2H), 6.53 (d, 1H, J=8.6 Hz), 6.48 (d, 1H, J=7.6 Hz), 4.74 (s, 2H), 4.38 (dd, 1H, J=12.4 Hz, J=3.2 Hz), 4.25 (dd, 1H, J=12.1 Hz, J=1.7 Hz), 3.84 (s, 2H), 3.41 (m, 1H), 3.16 (m, 2H), 2.99 (sept, 1H, J=6.8 Hz), 2.16 (s, 6H), 1.89 (m, 2H), 1.56 (m, 2H), 1.08 (d, 6H, J=6.6 Hz). HRMS exact mass calcd for $C_{26}H_{36}N_1O_4[M+H^+]^+$: m/z 426.26389. Found m/z 426.26465.

Example 24—(R)-1-aminopropan-2-yl 2-(4-(4-hydroxy-3-isopropylbenzyl)-3,5-dimethylphenoxy)acetate (Compound 28)

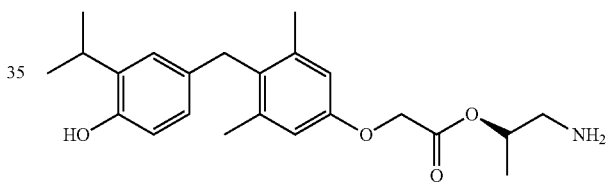

To a 0° C. solution of benzyl (R)-(2-hydroxypropyl) carbamate (262 mg, 1.25 mmol), DMAP (183 mg, 1.5 mmol), and THF (8 mL) was slowly added a solution of the acid chloride generated from 6 (0.5 mmol) in 4 mLTHF. The reaction mixture was allowed to warm to room temperature, then heated to 50° C. overnight with stirring. Filtration and evaporation of the resulting filtrate gave a light-yellow oil which was purified using flash chromatography (silica, 10% to 30% ethyl acetate/hexanes). The resulting ester (50 mg, 0.082 mmol, 17% yield) was dissolved in 5 mL of dry methanol with 1 mL THF and 10% Pd/C (40 mg) was added to generate a suspension. The reaction mixture was subjected to vacuum for approximately 1 min, then placed under argon for approximately 1 min. This process was repeated three times to ensure the mixture was properly degassed. Triethylsilane (0.4 mL, 2.51 mmol) was then added dropwise to the suspension and the reaction mixture was stirred for 4 hrs at room temperature. Filtration over a pad of celite with methanol and concentration in vacuo gave an oily residue which was precipitated with cold hexanes and washed with hexanes to give the desired product as a white solid (22 mg, 0.057 mmol, 68% yield, 12% overall yield). $^1$H NMR (400 MHz, CD$_3$OD): δ 6.77 (s, 1H), 6.62 (s, 2H), 6.55 (d, 1H, J=8.11 Hz), 6.45 (d, 1H, J=8.22 Hz), 5.20 (m, 1H, J=3.0 Hz), 4.71 (d, 2H, J=8.2 Hz), 3.84 (s, 2H), 3.21 (sept, 1H, J=6.8 Hz), 3.18 (m, 2H), 2.16 (s, 6H), 1.31 (d, 3H, J=6.5 Hz), 1.09 (d, 6H, J=6.99 Hz). HRMS exact mass calcd for $C_{23}H_{32}N_1O_4$ [M+H⁺]⁺: m/z 386.23258. Found m/z 386.23349.

Example 25—(S)-1-aminopropan-2-yl 2-(4-(4-hydroxy-3-isopropylbenzyl)-3,5-dimethylphenoxy)acetate (Compound 29)

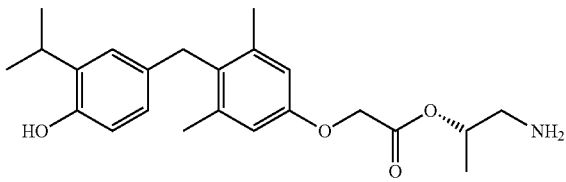

To a 0° C. solution of benzyl (S)-(2-hydroxypropyl)carbamate (262 mg, 1.25 mmol), DMAP (183 mg, 1.5 mmol), and THF (8 mL) was slowly added a solution of the acid chloride generated from 6 (0.5 mmol) in 4 mL THF. The reaction mixture was allowed to warm to room temperature, then heated to 50° C. overnight with stirring. Filtration and evaporation of the resulting filtrate gave a light-yellow oil which was purified using flash chromatography (silica, 10% to 30% ethyl acetate/hexanes). The resulting ester (101 mg, 0.166 mmol, 33% yield) was dissolved in 5 mL of dry methanol with 1 mL THF and 10% Pd/C (80 mg) was added to generate a suspension. The reaction mixture was subjected to vacuum for approximately 1 min, then placed under argon for approximately 1 min. This process was repeated three times to ensure the mixture was properly degassed. Triethylsilane (0.82 mL, 5.15 mmol) was then added dropwise to the suspension and the reaction mixture was stirred for 4 hrs at room temperature. Filtration over a pad of celite with methanol and concentration in vacuo gave an oily residue which was precipitated with cold hexanes and washed with hexanes to give the desired product as a white solid (59 mg, 0.153 mmol, 90% yield, 30% overall yield). ¹H NMR (400 MHz, CD₃OD): δ 6.77 (s, 1H), 6.61 (s, 2H), 6.54 (d, 1H, J=8 Hz), 6.48 (d, 1H, J=8.3 Hz), 5.19 (m, 1H, J=3 Hz), 4.70 (s, 2H, J=4 Hz), 3.84 (s, 2H), 3.19 (m, 2H), 3.16 (sept, 1H, J=6.8 Hz), 2.16 (s, 6H), 1.31 (d, 3H, J=6.4 Hz), 1.09 (d, 6H, J=6.9 Hz). HRMS exact mass calcd for $C_{23}H_{32}N_1O_4$ [M+H⁺]⁺: m/z 386.23258. Found m/z 386.23287.

Example 26—3-amino-1,1,1-trifluoropropan-2-yl 2-(4-(4-hydroxy-3-isopropylbenzyl)-3,5-dimethylphenoxy)acetate (Compound 30)

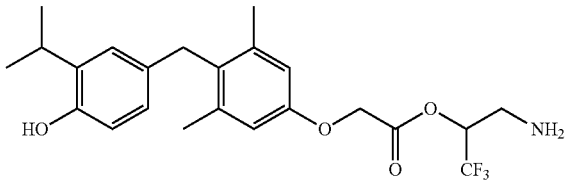 [SMILES: Cc1cc(OCC(=O)OC(CN)C(F)(F)F)cc(C)c1Cc1ccc(O)c(C(C)C)c1]

To a 0° C. solution of benzyl (3,3,3-trifluoro-2-hydroxypropyl)carbamate (207 mg, 0.786 mmol), DMAP (120 mg, 0.982 mmol), and chloroform (8 mL) was slowly added a solution of the acid chloride generated from 6 (0.392 mmol) in 4 mL chloroform. The reaction mixture was allowed to warm to room temperature, then heated to 50° C. overnight with stirring. Evaporation of the product mixture gave a light-yellow oil which was purified using flash chromatography (silica, 10% to 30% ethyl acetate/hexanes). The resulting ester (79 mg, 0.119 mmol, 30% yield) was dissolved in 5 mL of dry methanol with 1 mL THF and 10% Pd/C (80 mg) was added to generate a suspension. The reaction mixture was subjected to vacuum for approximately 1 min, then placed under argon for approximately 1 min. This process was repeated three times to ensure the mixture was properly degassed. Triethylsilane (0.6 mL, 3.77 mmol) was then added dropwise to the suspension and the reaction mixture was stirred for 4 hrs at room temperature. Filtration over a pad of celite with methanol and concentration in vacuo gave an oily residue which was precipitated with cold hexanes and washed with hexanes to give the desired product as a white solid (39 mg, 0.089 mmol, 75% yield, 23% overall yield). ¹H NMR (400 MHz, CD₃OD): δ 6.78 (s, 1H), 6.59 (s, 2H), 6.55 (d, 1H, J=8.1 Hz), 6.48 (d, 1H, J=8.4 Hz), 4.64 (s, 2H), 4.28 (m, 1H), 3.84 (s, 2H), 3.23 (dd, 1H, J=13.1 Hz, J=3.2 Hz), 3.17 (sept, 1H, J=6.9 Hz), 3.04 (dd, 1H, J=13.2 Hz, J=9.5 Hz), 2.15 (s, 6H), 1.09 (d, 6H, J=7 Hz).

Example 27—2-(methylamino)ethyl 2-(4-(4-hydroxy-3-methylbenzyl)-3,5-dimethylphenoxy)acetate hydrochloride (Compound 31)

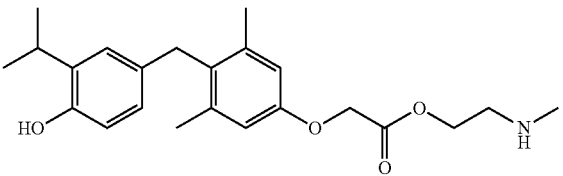

To a 0° C. solution of benzyl (2-hydroxyethyl)(methyl)carbamate (314 mg, 1.5 mmol), DMAP (183 mg, 1.5 mmol), and THF (8 mL) was slowly added a solution of the acid chloride generated from 6 (0.5 mmol) in 4 mL THF. The reaction mixture was allowed to warm to room temperature, then heated to 50° C. overnight with stirring. Filtration and evaporation of the resulting filtrate gave a light-yellow oil which was purified using flash chromatography (silica, 10% to 30% ethyl acetate/hexanes). The resulting ester (146 mg, 0.239 mmol, 48% yield) was dissolved in 5 mL of dry methanol with 1 mL THF and 10% Pd/C (100 mg) was added to generate a suspension. The reaction mixture was subjected to vacuum for approximately 1 min, then placed under argon for approximately 1 min. This process was repeated three times to ensure the mixture was properly degassed. Triethylsilane (1.2 mL, 7.53 mmol) was then added dropwise to the suspension and the reaction mixture was stirred for 4 hrs at room temperature. Filtration over a pad of celite with methanol and concentration in vacuo gave an oily residue which was precipitated with cold hexanes and washed with hexanes. The resulting residue was dissolved in 3 mL of ethyl acetate and 1 mL of 1 N HCl (ethyl acetate) was added and stirred 3 hrs. Evaporation of the solvent, followed by washing with hexanes gave the desired product as a white solid (37 mg, 0.088 mmol, 37% yield, 18% overall yield). ¹H NMR (400 MHz, CD₃CN): δ 8.87 (bs, 1H), 6.91 (s, 1H), 6.68 (s, 2H), 6.64 (d, 1H, J=8.1 Hz), 6.53 (d, 1H, J=7.8 Hz), 4.79 (s, 2H), 4.48 (m, 2H), 3.86 (s, 2H), 3.20 (m, 2H), 3.17 (sept, 1H, J=6.9 Hz), 2.60 (s, 3H), 2.19 (s, 6H), 1.13 (d, 6H, J=7.0 Hz). HRMS exact mass calcd for C$_{23}$H$_{32}$N$_1$O$_4$ [M+H$^+$]$^+$: m/z 386.23258. Found m/z 386.23259.

Example 28—1-aminopropan-2-yl 2-(4-(4-hydroxy-3-isopropylbenzyl)-3,5-dimethylphenoxy)acetate (Compound 32)

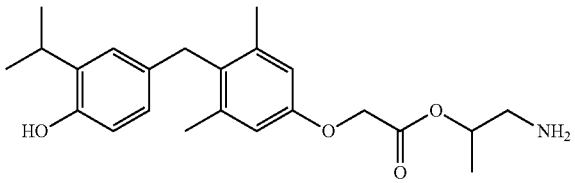

Followed procedure for the synthesis of (22) except with N-boc-1-amino-2-propanol and yielded an oil (2.2 mg, 0.0052 mmol, 2.1%): $^1$H NMR (methanol-d$_4$, 400.2 MHz) δ 6.75 (s, 1H), 6.54 (m, 3H), 6.47 (dd, 1H, J=2.0, 6.0 Hz), 5.18 (m, 1H), 4.69 (d, 2H, J=4.8 Hz), 3.84 (s, 2H), 3.15 (m, 3H), 2.15 (s, 6H), 1.30 (d, 3H, J=6.4 Hz), 1.07 (d, 6H, J=6.8 Hz). HRMS exact mass calcd for C$_{23}$H$_{32}$N$_1$O$_4$ [M+H$^+$]$^+$: m/z 386.23258. Found m/z 386.23308.

Example 29—1-(dimethylamino)propan-2-yl 2-(4-(4-hydroxy-3-isopropylbenzyl)-3,5-dimethylphenoxy)acetate (Compound 33)

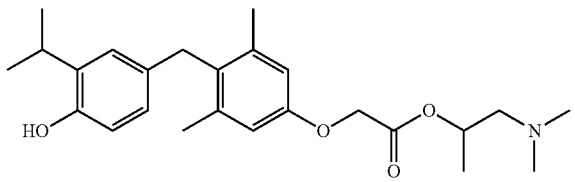 [SMILES: Cc1cc(OCC(=O)OC(C)CN(C)C)cc(C)c1Cc1ccc(O)c(C(C)C)c1]

A round bottom flask with a stirring bar and DCM (12 mL) is charged with 6 (669 mg, 1.6 mmol, 1 eq). It was cooled to 0° C. with an ice-bath and DMF (2 µL) was added to it. A solution of oxalyl chloride (640 µL, 7.45 mmol, 4.66 eq) in DCM (6 mL) was added to it dropwise. The reaction mixture was stirred at room temperature for 3 hours. The reaction mixture was then concentrated under reduced pressure and most of the excess oxalyl chloride was removed by repeated evaporation with DCM (2×10 mL). The crude acid chloride thus prepared was then dissolved in dry THF (5 mL) and slowly added to a 0° C. solution of 1-Dimethylamino-2-propanol (783 µL, 6.46 mmol) and DMAP (525 mg, 4.30 mmol) in THF (25 mL). The reaction mixture was then allowed to warm up at room temperature and refluxed overnight. It was then cooled, filtered and concentrated. The crude mixture was purified by flash chromatography (silica, 0% to 5% MeOH/DCM) to yield the pure benzyl protected GC1 ester. The resulting protected ester (150 mg, 0.298 mmol) was dissolved in a mixture of THF and MeOH (1:10). 10% Pd/C (30 mg, 0.2 eq) was added to it followed by the dropwise addition of triethylsilane (684 µL, 4.47 mmol). After stirring at room temperature for 2 hours, the reaction mixture was filtered over a bed of celite and concentrated. Purification on silica using flash chromatography and 0% to 5% MeOH in DCM as the eluent gave the dimethyl propanol-GC1 ester 33 (25 mg, 20%). 1H NMR (400 MHz, CD3CN): δ 6.92 (d, 1H, J=1.84 Hz), 6.60 (m, 4H), 5.25 (m, 1H), 4.66 (m, 3H), 3.89 (s, 2H), 3.15 (m, 1H), 2.34 (s, 6H), 2.12 (s, 6H), 1.29 (d, 3H, J=6.4 Hz), 1.21 (d, 6H, J=6.8 Hz). LRMS for C$_{25}$H$_{35}$NO$_4$ [M+H$^+$]$^+$: m/z 414.3. Found m/z 414.9.

Example 30—1-(1H-imidazol-1-yl)propan-2-yl 2-(4-(4-hydroxy-3-isopropylbenzyl)-3,5-dimethylphenoxy)acetate (Compound 34)

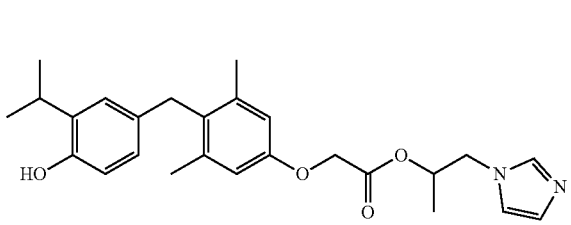 [SMILES: Cc1cc(OCC(=O)OC(C)Cn2ccnc2)cc(C)c1Cc1ccc(O)c(C(C)C)c1]

A stirring solution of 6 (100 mg, 0.239 mmol, 1 eq) in DCM (0.5 mL) at room temperature is treated with oxalyl chloride (125 µL, 1.43 mmol, 6 eq) and 1 drop of DMF. The reaction stirs for 3 hours followed by removal of the solvent under reduced pressure. The crude intermediate is dissolved in DCM (3 mL), which is subsequently removed under reduced pressure. The remainder oxalyl chloride was removed by repeated evaporation with DCM (2×10 mL). The crude intermediate acyl chloride is treated with DCM (1 mL) followed by triethylamine (65 µL, 0.478 mmol, 2 eq) and 2-(1H-imidazol-1-yl)propan-1-ol (72 mg, 0.57 mmol, 2.4 eq). 2-(1H-imidazol-1-yl)propan-1-ol was synthesized as previously described in Borowiecki, P. et al. *Beilstein J Org Chem*, 9, 516-525 (2013). The reaction stirs overnight at room temperature and is then purified directly by flash chromatography (0-5% MeOH in DCM) and dried under high vacuum to give the intermediate ester as a viscous oil (78 mg, 62%). A stirring solution of this intermediate ester (78 mg, 0.148 mmol, 1 eq) in degassed THF:MeOH (1:1, 1 mL) under argon is treated with 10% Pd/C (20 mg) followed by dropwise addition of triethylsilane (70 mg, 0.59 mmol, 4 eq). The reaction stirs for 3 hours at room temperature. The reaction solution is filtered through a pad of celite, which is subsequently washed with MeOH. The filtrate is concentrated and then purified by flash chromatography (0-10% MeOH in DCM) to give the product 34 as a white solid (32 mg, 50%). $^1$H NMR (400 MHz, Chloroform-d) δ 7.28 (b, 1H), 7.06 (s, 1H), 6.93 (d, J=2 Hz, 1H), 6.89 (s, 1H), 6.60 (m, 4H), 5.3 (m, 1H), 4.60 (s, 2H), 4.09 (m, 2H), 3.90 (s, 2H), 3.23 (sept, J=6.9, 1H), 2.22 (s, 6H), 1.25 (m, 9H). LRMS (ESI) m/z (M+H$^+$) C26H33N2O4 calculated 436.2, found 436.7.

Example 31—1-amino-1-oxopropan-2-yl 2-(4-(4-hydroxy-3-isopropylbenzyl)-3,5-dimethylphenoxy)acetate (Compound 35)

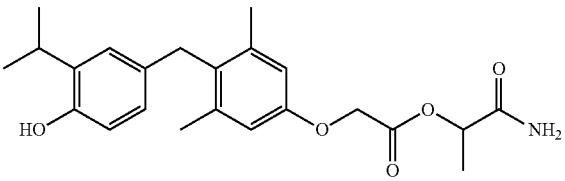 [SMILES: Cc1cc(OCC(=O)OC(C)C(N)=O)cc(C)c1Cc1ccc(O)c(C(C)C)c1]

A stirring solution of 6 (270 mg, 0.646 mmol, 1 eq) in DCM (4 mL) at 0° C. is treated with oxalyl chloride (221 μL, 2.58 mmol, 4 eq) and 1 drop of DMF. The reaction is warmed to room temperature and stirs for 3 hours followed by removal of the solvent under reduced pressure. The crude reaction is dissolved in DCM (10 mL), which is subsequently removed under reduced pressure. The remainder oxalyl chloride was removed by repeated evaporation with DCM (2×10 mL). The crude intermediate acyl chloride is treated with DCM (1 mL) followed by triethylamine (270 μL, 1.94 mmol, 3 eq), lactamide (115 mg, 1.31 mmol, 2 eq), and DMAP (8 mg, 0.065 mmol, 0.1 eq). The reaction stirs overnight at room temperature and is then purified directly by flash chromatography (0-5% MeOH in DCM) and dried under high vacuum to give the intermediate ester as a viscous oil (256 mg, 81%). A stirring solution of this ester (47 mg, 0.148 mmol, 1 eq) in degassed MeOH (1 mL) under argon is treated with 5% Pd/C (10 mg) followed by dropwise addition of triethylsilane (145 mg, 1.25 mmol, 13 eq). The reaction stirs for 3 hours at room temperature. The reaction solution is filtered through a pad of celite, which is subsequently washed with MeOH. The filtrate is concentrated and then purified by flash chromatography (0-5% MeOH in DCM) to give the product 35 as a white solid (27 mg, 70%). $^1$H NMR (400 MHz, Chloroform-d) δ 6.95 (d, J=2 Hz, 1H), 6.60 (m, 4H), 5.82 (b, 1H), 5.35 (q, J=6.9 Hz, 1H), 5.23 (b, 1H), 4.78 (b, 1H), 4.75 (s, 2H), 3.91 (s, 2H), 3.18 (sept, J=6.9 Hz, 1H), 2.22 (s, 6H), 1.54 (d, J=6.9 Hz, 3H), 1.23 (d, J=7 Hz, 6H). LRMS (ESI) m/z (M+Na$^+$) C23H29NO5Na requires 422.2, found 422.0.

Example 32—1-hydroxypropan-2-yl 2-(4-(4-hydroxy-3-isopropylbenzyl)-3,5-dimethylphenoxy) acetate (Compound 36)

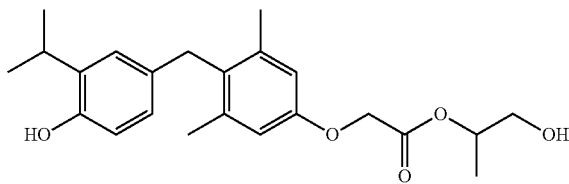 [SMILES: Cc1cc(OCC(=O)OC(C)CO)cc(C)c1Cc1ccc(O)c(C(C)C)c1]

A mixture of 6 (200 mg, 0.477 mmol, 1 eq) and 1-(benzyloxy)propan-2-ol (475 mg, 2.86 mmol, 6 eq) are treated neat with sulfuric acid (1 drop). 1-(benzyloxy)propan-2-ol was synthesized as previously described in Aikawa, K. et al. J Am Chem Soc, 134, 10329-10332 (2012). The reaction stirs for 3 days at room temperature. The crude reaction mixture is diluted with DCM (3 mL) and purified by flash chromatography (0-40% EtOAc in hexanes). The product is concentrated and dried under high vacuum to give the intermediate ester as a viscous oil (236 mg, 88%). A stirring solution of this ester (200 mg, 0.352 mmol, 1 eq) under argon is treated with 10% Pd/C (40 mg) and triethylsilane (340 μL, 2.12 mmol, 6 eq) is added dropwise. The reaction stirs at room temperature for 3 hours. The reaction solution is filtered through a pad of celite, which is subsequently washed with MeOH. The filtrate is concentrated and then purified by flash chromatography (0-5% MeOH in DCM) to give the product 36 that solidifies upon exposed to air (77 mg, 56%). The isolated product was shown to be a mixture of 1- and 2-hydroxypropanyl regioisomers (3:1); the characterization of only the major isomer is shown. $^1$H NMR (400 MHz, Chloroform-d) δ 6.93 (d, J=2 Hz, 1H), 6.60 (m, 4H), 5.15 (qd, J=6.5 Hz, 3.3 Hz, 1H), 4.66 (s, 2H), 4.58 (s, 1H), 4.13 (b, 1H), 3.91 (s, 2H), 3.69 (m, 2H), 3.16 (sept, J=6.9 Hz, 1H), 2.22 (s, 6H), 1.249 (m, 9H). LRMS (ESI) m/z (M+Na$^+$) C23H30O5Na calculated 409.2, found 408.7.

Example 33—3-methyl-1-(methylamino)butan-2-yl 2-(4-(4-hydroxy-3-isopropylbenzyl)-3,5-dimethylphenoxy)acetate (Compound 37)

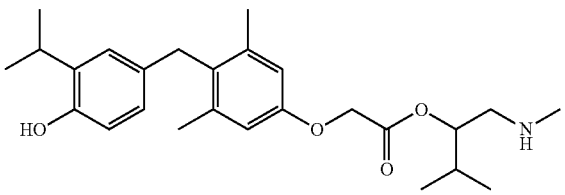 [SMILES: CNCC(OC(=O)COc1cc(C)c(Cc2ccc(O)c(C(C)C)c2)c(C)c1)C(C)C]

To a 0° C. solution of 1-(benzyl(methyl)amino)-3-methylbutan-2-ol (530 mg, 2.56 mmol), DMAP (312 mg, 2.55 mmol), and THF (8 mL) was slowly added a solution of the acid chloride generated from 6 (0.66 mmol) in 4 mL THF. The reaction mixture was allowed to warm to room temperature, then heated to reflux overnight with stirring. Filtration and evaporation of the resulting filtrate gave a light-yellow oil which was purified using flash chromatography (silica, 10% to 50% ethyl acetate/hexanes). The resulting ester (200 mg, 0.329 mmol, 50% yield) was dissolved in 5 mL of dry methanol with 1 mL THF and 10% Pd/C (100 mg) was added to generate a suspension. The reaction mixture was subjected to vacuum for approximately 1 min, then placed under argon for approximately 1 min. This process was repeated three times to ensure the mixture was properly degassed. Triethylsilane (1.6 mL, 10.04 mmol) was then added dropwise to the suspension and the reaction mixture was stirred for 4 hrs at room temperature. Filtration over a pad of celite with methanol and concentration in vacuo gave an oily residue which was precipitated with cold hexanes and washed with hexanes. The desired product was obtained as a white solid after drying under high vacuum (101 mg, 0.236 mmol, 72% yield, 36% overall yield). $^1$H NMR (400 MHz, CD$_3$CN): δ 6.93 (s, 1H), 6.71 (s, 2H), 6.69 (d, 1H, J=8.6 Hz), 6.54 (dd, 1H, J=8.3 Hz, J=2.2 Hz), 5.22 (m, 1H), 5.12 (d, 1H, J=16.5 Hz), 4.77 (d, 1H, J=16.5 Hz), 3.88 (s, 2H), 3.18 (m, 3H), 2.62 (s, 3H), 2.20 (s, 6H), 1.15 (d, 6H, J=6.8 Hz), 0.93 (dd, 6H, J=7 Hz, J=2.1 Hz). LRMS (ESI) m/z C$_{26}$H$_{37}$NO$_4$ calculated (M+H$^+$) 428.3, found 428.7.

Example 34—1-amino-3-methylbutan-2-yl 2-(4-(4-hydroxy-3-isopropylbenzyl)-3,5-dimethylphenoxy) acetate (Compound 38)

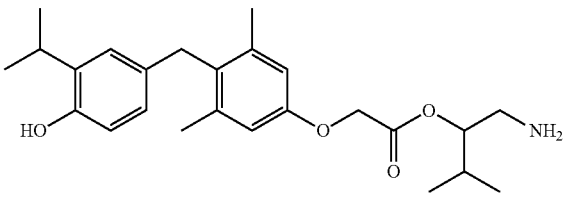 [SMILES: Cc1cc(OCC(=O)OC(CN)C(C)C)cc(C)c1Cc1ccc(O)c(C(C)C)c1]

To a 0° C. solution of 1-(dibenzylamino)-3-methylbutan-2-ol (745 mg, 2.63 mmol), DMAP (321 mg, 2.63 mmol), and THF (8 mL) was slowly added a solution of the acid chloride generated from 6 (0.66 mmol) in 4 mL THF. The reaction mixture was allowed to warm to room temperature, then heated to reflux overnight with stirring. Filtration and evaporation of the resulting filtrate gave a light-yellow oil which was purified using flash chromatography (silica, 10% to 50% ethyl acetate/hexanes). The resulting ester (128 mg, 0.187 mmol, 28% yield) was dissolved in 5 mL of dry methanol with 1 mL THF and 10% Pd/C (100 mg) was added to generate a suspension. The reaction mixture was subjected to vacuum for approximately 1 min, then placed under argon for approximately 1 min. This process was repeated three times to ensure the mixture was properly degassed. Triethylsilane (1.35 mL, 8.47 mmol) was then added dropwise to the suspension and the reaction mixture was stirred for 4 hrs at room temperature. Filtration over a pad of celite with methanol and concentration in vacuo gave an oily residue which was precipitated with cold hexanes and washed with hexanes. The desired product was obtained as a white solid after drying under high vacuum (69 mg, 0.167 mmol, 89% yield, 25% overall yield). $^1$H NMR (400 MHz, CD$_3$CN): δ (s, 1H), 6.69 (s, 2H), 6.66 (d, 1H, J=8.5 Hz), 6.53 (dd, 1H, J=8.1 Hz, J=2.5 Hz), 5.12 (m, 1H), 5.03 (d, 1H, J=16.3 Hz), 4.75 (d, 1H, J=16.5 Hz), 3.87 (s, 2H), 3.18 (m, 3H), 2.20 (s, 6H), 1.15 (d, 6H, J=6.8 Hz), 0.92 (dd, 6H, J=6.8 Hz, J=1.7 Hz). LRMS (ESI) m/z C25H35NO4 calculated (M+H$^+$): 414.3, found: 414.4.

The invention claimed is:

1. A pharmaceutical composition comprising one or more pharmaceutically acceptable carriers and an effective amount of a compound with the structure:

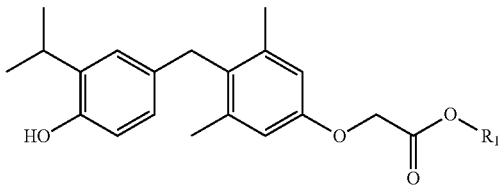

or any pharmaceutically acceptable salt thereof, where R$_1$ is heteroalkyl, substituted heteroalkyl, substituted cycloalkyl, heterocycloalkyl, substituted heterocycloalkyl, substituted aryl, heteroaryl, or substituted heteroaryl.

2. A pharmaceutical composition comprising one or more pharmaceutically acceptable carriers and an effective amount of a compound with the structure:

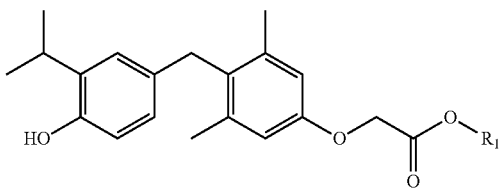

or any pharmaceutically acceptable salt thereof where R$_1$ is lysinyl, valinyl, phenylalaninyl, glucosyl, or

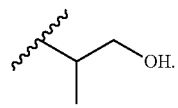 [SMILES: *C(C)CO]

3. A pharmaceutical composition comprising one or more pharmaceutically acceptable carriers and an effective amount of a compound with the structure:

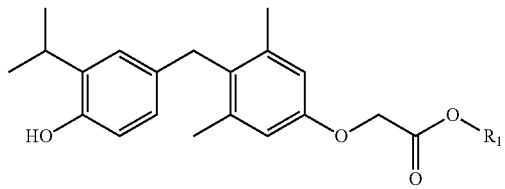

or any pharmaceutically acceptable salt thereof where R$_1$ is substituted alkylamino, cycloalkylamino, or substituted cycloalkylamino.

4. A pharmaceutical composition comprising one or more pharmaceutically acceptable carriers and an effective amount of a compound with the structure:

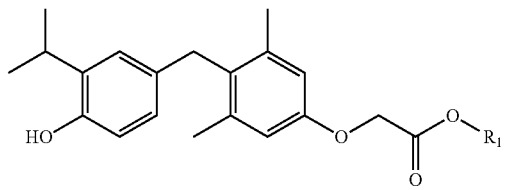

or any pharmaceutically acceptable salt thereof wherein R$_1$ is ethylamino, ethyl(N,N,N)-trimethylamino, ethylmorpholinyl, ethyl(N,N)-dimethylamino, 3-(N-methyl)azetidinyl, 4-pyrrolidinyl, 3-pyrrolidinyl, 2,2-dimethylethylamino, 3-(3-trifluoromethyl)azetidinyl, 2-pyrrolidinyl, 2-methylethylamino, 2-trifluoromethylamino, N-methyl-ethylamino, 1-methyl-(N,N)-dimethylethylamino, 1-methyl-2-imazodinylethylamino; 1-methyl-2-keto-ethylamino, 1-isopropyl-ethylamino, or 1-isopropyl-N-methyl-ethylamino.

5. The pharmaceutical composition of claim 4 wherein R$_1$ is 2-methylethylamino further comprising R and S enantiomers.

6. A pharmaceutical composition comprising one or more pharmaceutically acceptable carriers and an effective amount of a compound, wherein the compound is 2-(dimethylamino)ethyl 2-(4-{[4-hydroxy-3-(propan-2-yl)phenyl]methyl}-3,5-dimethylphenoxy)acetate; 1-methylazetidin-3-yl 2-(4-{[4-hydroxy-3-(propan-2-yl)phenyl]methyl}-3,5-dimethylphenoxy)acetate; pyrrolidin-2-ylmethyl 2-(4-{[4-hydroxy-3-(propan-2-yl)phenyl]methyl}-3,5-dimethylphenoxy)acetate; 3-methylazetidin-3-yl 2-(4-{[4-hydroxy-3-(propan-2-yl)phenyl]methyl}-3,5-dimethylphenoxy)acetate; piperidin-4-yl 2-(4-{[4-hydroxy-3-(propan-2-yl)phenyl]methyl}-3,5-dimethylphenoxy) acetate; piperidin-4-yl 2-(4-{[4-hydroxy-3-(propan-2-yl)phenyl]methyl}-3,5-dimethylphenoxy)acetate; 1-amino-2-methlpropan-2-yl 2-(4-{[4-hydroxy-3-(propan-2-yl)phenyl]methyl}-3,5-dimethylphenoxy)acetate; 3-(trifluoromethyl)azetidin-3-yl 2-(4-{[4-hydroxy-3-(propan-2-yl)phenyl]methyl}-3,5-dimethylphenoxy)acetate; 2-((2-(4-(4- hydroxy-3-isopropylbenzyl)-3,5-dimethylphenoxy)acetoxy)methyl)piperidin-1-ium chloride; (R)-1-aminopropan-2-yl 2-(4-(4-hydroxy-3-isopropylbenzyl)-3,5-dimethylphenoxy)acetate; (S)-1-aminopropan-2-yl 2-(4-(4-hydroxy-3-isopropylbenzyl)-3,5-dimethylphenoxy)acetate; 2-(methylamino)ethyl 2-(4-(4-hydroxy-3-methylbenzyl)-3,5-dimethylphenoxy)acetate hydrochloride; 1-aminopropan-2-yl 2-(4-(4-hydroxy-3-isopropylbenzyl)-3,5-dimethylphenoxy)acetate; 1-(dimethylamino)propan-2-yl 2-(4-(4-hydroxy-3-isopropylbenzyl)-3,5-dimethylphenoxy)acetate; 1-(1H-imidazol-1-yl)propan-2-yl 2-(4-(4-hydroxy-3-isopropylbenzyl)-3,5-dimethylphenoxy)acetate; 1-amino-1-oxopropan-2-yl 2-(4-(4-hydroxy-3-isopropylbenzyl)-3,5-dimethylphenoxy)acetate, 1-hydroxypropan-2-yl 2-(4-(4-hydroxy-3-isopropylbenzyl)-3,5-dimethylphenoxy)acetate; 3-methyl-1-(methylamino)butan-2-yl 2-(4-(4-hydroxy-3-isopropylbenzyl)-3,5-dimethylphenoxy)acetate; or 1-amino-3-methylbutan-2-yl 2-(4-(4-hydroxy-3-isopropylbenzyl)-3,5-dimethylphenoxy)acetate.

7. The pharmaceutical composition of claim 4, wherein the compound has the structure:

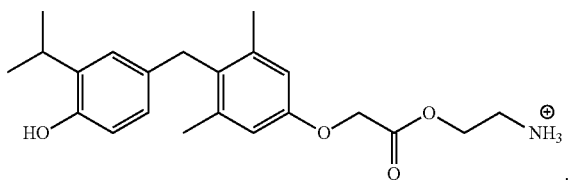 [SMILES: Cc1cc(OCC(=O)OCC[NH3+])cc(C)c1Cc1ccc(O)c(C(C)C)c1]

and wherein the compound is a halide salt.

8. The pharmaceutical composition of claim 4, wherein the compound has the structure:

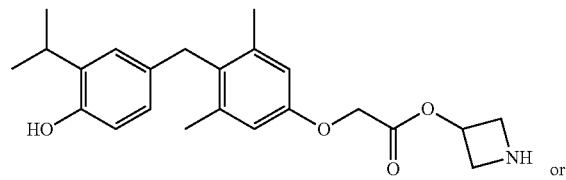

or

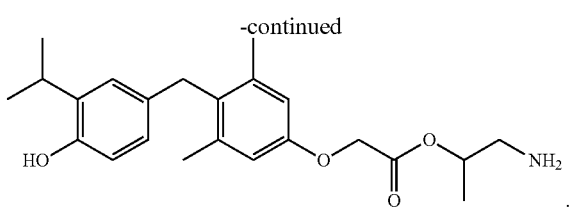

9. The pharmaceutical composition of claim 7 with the structure:

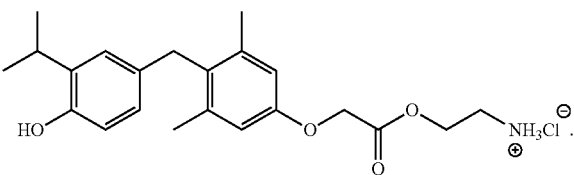

10. A compound with the structure:

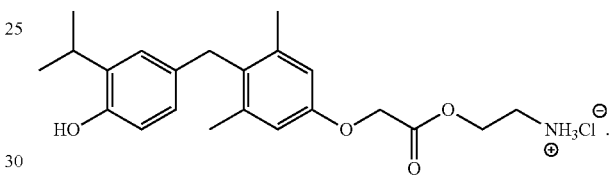

11. A compound with the structure:

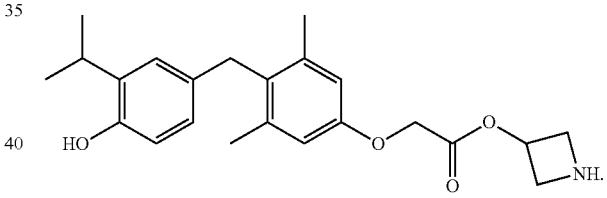

* * * * *